US010112984B2

(12) United States Patent
Van Wyk et al.

(10) Patent No.: US 10,112,984 B2
(45) Date of Patent: Oct. 30, 2018

(54) LIGHT-SENSITIVE CHIMERIC GPCR PROTEIN

(75) Inventors: Michiel Van Wyk, Hinterkappelen (CH); Sonja Kleinlogel, Hinterkappelen (CH)

(73) Assignee: Haagstreit Medtech AG, Koniz (CH)

( * ) Notice: Subject to any disclaimer, the term of this patent is extended or adjusted under 35 U.S.C. 154(b) by 64 days.

(21) Appl. No.: 14/128,155

(22) PCT Filed: Jun. 22, 2012

(86) PCT No.: PCT/CH2012/000138
§ 371 (c)(1),
(2), (4) Date: Feb. 27, 2014

(87) PCT Pub. No.: WO2012/174674
PCT Pub. Date: Dec. 27, 2012

(65) Prior Publication Data
US 2014/0171376 A1    Jun. 19, 2014

Related U.S. Application Data

(60) Provisional application No. 61/500,863, filed on Jun. 24, 2011.

(51) Int. Cl.
| | |
|---|---|
| *A61K 38/00* | (2006.01) |
| *C07K 14/72* | (2006.01) |
| *C07K 14/705* | (2006.01) |
| *A61P 9/10* | (2006.01) |
| *A61P 27/02* | (2006.01) |
| *C07K 14/00* | (2006.01) |
| *C07K 17/00* | (2006.01) |
| *A61K 38/16* | (2006.01) |

(52) U.S. Cl.
CPC .......... *C07K 14/705* (2013.01); *A61K 38/16* (2013.01); *C07K 14/723* (2013.01)

(58) Field of Classification Search
None
See application file for complete search history.

(56) References Cited

U.S. PATENT DOCUMENTS

| | | |
|---|---|---|
| 2005/0208022 A1 | 9/2005 | Masland |
| 2009/0088399 A1 | 4/2009 | Balya et al. |
| 2009/0181454 A1* | 7/2009 | Trauner ............... C09B 56/08 435/325 |
| 2009/0208462 A1 | 8/2009 | Hankins et al. |
| 2010/0015095 A1 | 1/2010 | Pan et al. |
| 2012/0093772 A1* | 4/2012 | Horsager et al. ........... 424/93.2 |

FOREIGN PATENT DOCUMENTS

| | | |
|---|---|---|
| EP | 1 891 976 A1 | 2/2008 |
| WO | 2006/059081 A2 | 6/2006 |

OTHER PUBLICATIONS

Tsukamoto et al., Photochem. Photobiol. 9:1435-1443 (2010).*
Yamashita et al., J. Biochem. 130:149-155 (2001).*
Enz, BioEssays 29:60-73 (2006).*
BLAST sequence comparison between mouse mGluR6, Accession No. AAH41684.1, and mouse melanopsin, Accession No. AAF24979.1, performed on Jun. 21, 2016.*
NCBI Database, GenBank Accession No. AAH41684.1, mouse mGluR6 amino acid sequence, 2 pages (2006).*
NCBI Database, GenBank Accession No. AAF24979.1, mouse melanopsin amino acid sequence, 2 pages (2000).*
Levitz et al., Nat. Neurosci. 16:507-516 (2013).*
Rost, Protein Eng. 12:85-94 (1999) (Year: 1999).*
Peirson et al., Neuron 49:331-339 (2006) (Year: 2006).*
"Chimeric protein", available online at https://medical-dictionary.thefreedictionary.com/chimeric+protein, 2 pages (accessed on Oct. 24, 2017) (Year: 2017).*
Shichida et al., Phil. Trans. R. Soc. B 364:2881-2895 (2009) (Year: 2009).*
University of Houston, Federal Circuit Patent Law Case Update, *Capon v Eshhar*, available online at http://www.law.uh.edu/faculty/gvetter3/fcplc/CaseSummaries/2005/Capon%20v.%20Eshhar%20v.%20Dudas,%2003-1480%20(Fed.%20Cir.%20Aug.%2012,%202005)%20%5BSUMMARY%5D.pdf, 1 page (2005) (Year: 2005).*

(Continued)

*Primary Examiner* — James H Alstrum-Acevedo
*Assistant Examiner* — Thea D' Ambrosio
(74) *Attorney, Agent, or Firm* — Larson & Anderson, LLC

(57) ABSTRACT

A light-sensitive chimeric protein includes domains from at least two members of the G-protein-coupled-receptor (GPCR) protein super family, which are fused to yield a light-sensitive GPCR chimera capable of coupling a light signal to the signaling cascade of the metabotropic glutamate receptor 6 (mGluR6) is provided for medical therapy and pharmaceuticals for treating loss of vision, in particular resulting from retinal photoreceptor degeneration. A first GPCR family member contributes domains which mediate the light-sensitivity to the chimeric light-sensitive GPCR protein and belongs to the family of light-sensitive GPCR proteins also called photopigments. In some cases, the GPCR protein is melanopsin, in particular human melanopsin. A second of the at least two GPCR family members is mGluR6, which contributes domains for coupling the light signal to the intracellular signaling cascade of mGluR6, which is a native component of the cell membrane of ON-bipolar cells in the inner retina.

23 Claims, 3 Drawing Sheets
Specification includes a Sequence Listing.

(56) References Cited

OTHER PUBLICATIONS

Bainbridge, J. et al. "Effect of Gene Therapy on Visual Function in Leber's Congenital Amaurosis", The New England Journal of Medicine, 2008, pp. 2231-2239, vol. 358, No. 21.
Buch, P. et al. "AAV-mediated gene therapy for retinal disorders: from mouse to man", Gene Therapy, 2008, pp. 849-857, vol. 15.
Database OMIM "Glutamate receptor, metabotropic, 6, GRM6",Sep. 25, 2012 retrieved from NCBI Databse accession No. 604096.
Fradot, M. et al. "Gene Therapy in Ophthalmology: Validation on Cultured Retinal Cells and Explants from Postmortem Human Eyes", Human Gene Therapy, 2011, pp. 587-593, vol. 22.
Hartong, D. et al. "Retinitis pigmentosa", Lancet, 2006, pp. 1795-1809, vol. 368.
Hermann, R. et al. "Predicted 3D-structure of melanopsin, the non-rod, non-cone photopigment of the mammalian circadian clock, from Djungarian hamsters (*Phodopus sungorus*)", Neuroscience Letters, 2005, pp. 76-80, vol. 376.
Huang, W. et al. "Cell type-specific and light dependent expression of Rab1 and Rab6 GTpases in mammalian retinas", Vis. Neuroscience, 2009, pp. 443-452, vol. 26, Nos. 5-6.
Ivanova, E. et al. "Evaluation of AAV-Mediated Expression of Chop2-GFP in the Marmoset Retina", Investigative Ophthalmology & Visual Science, 2010, pp. 5288-5296, vol. 51, No. 10.
Jacobson, S. et al. "Gene Therapy for Leber Congenital Amaurosiss Caused by RPE65 Mutations", Arch Ophthalmol., 2012, pp. 9-24, vol. 130, No. 1.
Kiefer, F. et al. "The Swiss-Model Repository and associated resources", Nucleic Acids Research, 2009, pp. D387-D392, vol. 37.
Kim, D. et al. "A Core Paired-Type and POU Homeodomain-Containing Transcription Factor Program Drives Retinal Bipolar Cell Gene Expression", The Journal of Neuroscience, 2008, pp. 7748-7764, vol. 28, No. 31.
Krizaj, D. et al. "Plasticity of TRPM1 expression and localization in the wild type and degenerating mouse retina", Vision research, 2010, pp. 2460-2465, vol. 50.
Lagali, P. et al. "Light-activated channels targeted to ON bipolar cells restore visual function in retinal degeneration", Nature Neuroscience, 2008, pp. 667-675, vol. 11, No. 6.
Matsuda, T. et al. "Electoporation and RNA interference in the rodent retina in vivo and in vitro", PNAS, 2004, pp. 16-22, vol. 101, No. 1.
Pang, J. et al. "AAV-Mediated Gene Therapy for Retinal Degeneration in the rd10 Mouse Containing a Recessive PDEβ Mutation", Investigative Ophthalmology & Visual Science, 2008, pp. 4278-4283, vol. 49, No. 10.
Pang, J. et al. "Long-term Retinal Function and Structure Rescue using Capsid Mutant AAV8 Vector in the rd20 Mouse, a Model of Recessive Retinitis Pigmentosa", The American Society of Gene & Cell Therapy, 2011, pp. 234-242, vol. 19, No. 2.
Park, T. et al. "Intravitreal delivery of AAV8 retinoschhisin results in cell type-specific gene expression and retinal rescue in the Rs1-KO mouse", Gene Therapy, 2009, pp. 916-926, vol. 16.
Petrs-Silva, H. et al. "Novel Properties of Tyrosine-mutant AAV2 Vectors in the Mouse Retina", Molecular Therapy, 2011, pp. 293-301, vol. 19, No. 2.
Schmidt, T. et al. "Intrinsic and Extrinsic Light Responses in Melanopsin-Expressing Ganglion Cells During Mouse Development" J Neurophysiol, 2008, pp. 371-384, vol. 100.
Yamashita, T. et al "The Second Loop of Metabotropic Glutamate Receptor Functions at the Third Loop Position of Rhodopsin", J. Biochem., 2001, pp. 149-155, vol. 130.
Pires, S. S. et al., Differential Expression of Two Distinct Functional Isoforms of Melanopsin (Opn4) in the Mammalian Retina, The Journal of Neuroscience, 2009, pp. 12332-12342, vol. 29, No. 39.

\* cited by examiner

LIGHT-SENSITIVE CHIMERIC GPCR PROTEIN

FIELD OF THE INVENTION

The invention lies in the field of medical therapeutics and medical therapy for the treatment of human or animal patients suffering from loss of vision and concerns treatments and the manufacture of medicaments for improving vision, in particular for treating loss of vision resulting from retinal photoreceptor degeneration with a light-sensitive chimeric GPCR protein.

BACKGROUND OF THE INVENTION

Major causes of retinal photoreceptor degeneration include retinitis pigmentosa (RP), age-related macular degeneration (ARMD), diabetic retinopathy and other diseases. Approximately one in three thousand, or three million people worldwide, suffer from retinitis pigmentosa (RP), a genetic condition that leads to photoreceptor degeneration and eventually blindness. The rate and severity of photoreceptor degeneration is variable and highly dependant on the mutation itself. Over fifty genes may be affected (Hartong et al. Lancet 368:1795-1809; 2006). To date, little treatment is available for RP patients. Ongoing trials that focus on neuroprotective agents (e.g. ciliary neurotrophic factor) or gene addition therapy (introducing the "non-mutated" gene), which aim to correct acquired or hereditary gene deficiencies to the natural functional gene, have so far shown only marginal success. Given that the adult retina has no ability to generate new photoreceptors after photoreceptor loss, gene addition therapy is only useful as long as photoreceptor loss is small and mainly slows down or stabilizes the early condition.

An alternative approach employed in recent experimental studies is to render the remaining photoreceptors or surviving inner retinal neurons light-sensitive through transgenic expression of a light-sensitive protein.

In US 2009/0088399 and US 2010/0015095 it is proposed to introduce the light-gated algal ion-channel channelrhodopsin-2 (ChR2) into the inner retina of patients suffering from photoreceptor cell degeneration This renders the naturally light-insensitive inner retinal cells, such as bipolar or amacrine cells, light-sensitive and capable of detecting visual information, which is subsequently relayed to the brain without receiving input from photoreceptors.

Similarly, in US 2005/0208022 and US 2009/0208462 it is proposed to introduce a photoreceptive protein such as an opsin (including melanopsin) or cytochromes into the inner retinal neurons including amacrine, horizontal and bipolar cells of patients suffering from photoreceptor degeneration.

The approach to express ChR2 in inner retinal neurons holds considerable promise and is currently tested in non-human primates (Fradot M et al. Human Gene Therapy 22(5), 587-593; 2011) and isolated human retinas (Ivanova E et al. Opthalmol Vis Sci 51(10), 5288-5296, 2010), raising hope for clinical trials in the near future.

In recent years retinal gene-replacement therapy using recombinant Adeno-associated virus (rAAV) has been successful and has reached final clinical trials. In particular, Bainbridge and colleagues used rAAV to replace the defective retinal pigment epithelium-specific 65-kDa protein gene (RPE65). A deficiency in the RPE65 protein renders photoreceptors unable to respond to light, as it is required for the recycling of the chromophore, i.e. the conversion of all-trans retinal to 11-cis retinal (Bainbridge J W B et al., N Engl J Med 358(21), 2231-2239; 2008). Gene therapy is therefore a promising therapeutic approach to correct for visual deficiencies by the introduction of suitable genes into retinal neurons.

The currently available light-activatable proteins that could be used in gene therapy to compensate for the loss of photoreceptor cells, however, still hold a number of substantial drawbacks: 1) Artificial expression of foreign, invertebrate or algal proteins, e.g. ChR2, could trigger unpredictable immune reactions in patients. 2) ChR2 has a relatively high permeability to calcium, which might be toxic over the long term. 3) The ChR2 response is inherently weak at natural light intensities as each captured photon can only activate a single protein. 4) Although, melanopsin is able to amplify light-signals by gating the activities of high-throughput enzymatic reactions, these enzymatic partners are not sufficiently available in inner retinal neurons. Therefore, the expression of melanopsin in ganglion cells and ON-bipolar cells does not elicit an amplification of the light signal sufficient to restore functional vision at natural light intensities. 5) Also, the regulatory mechanisms that naturally control protein activity through changes in turnover and modulation are absent when expressing foreign proteins.

The object of the current invention is to provide a light-sensitive chimeric protein, which, when expressed in inner retinal neurons, overcomes these deficiencies. That is, it is an object of the invention to provide a superior light-sensitive protein for the improvement and restoration of vision, particularly in patients with retinal photoreceptor degeneration. This chimeric protein will improve or restore light-sensitivity to a higher extent compared to the light-sensitivity that is obtainable by proteins proposed in the state of the art. Further objects of the invention include the genetic information encoding the chimeric light-sensitive protein and methods of expressing this chimeric protein in living cells and organisms. Yet further objects of the invention include the expression of the genetic information encoding the chimeric light-sensitive protein in inner retinal cells in vivo for therapeutic treatment and biomedical products comprising the light-sensitive protein or genetic information encoding the chimeric protein.

SUMMARY OF THE INVENTION

This technical problem is solved by a light-sensitive chimeric protein comprising domains from at least two members of the G-protein-coupled-receptor (GPCR) protein super family, which are fused to yield a light-sensitive GPCR chimera capable of coupling a light signal to the signaling cascade of the metabotropic glutamate receptor 6 (mGluR6).

The G-protein-coupled-receptor (GPCR) protein super family members are transmembrane protein receptors transmitting signals from the cell surface to intracellular effectors. They have a structure, which typically comprises seven transmembrane domains (TM1 to TM7), three extracellular loops (EL1 to EL3), three intracellular loops (IL1 to IL3), an extracellular N-terminal domain (NT) and an intracellular C-terminal (CT) domain. The GPCR protein super family includes light-sensitive receptor proteins called photopigments such as opsins, for example rhodopsin and melanopsin. The GPCR super family also include ligand-gated metabotropic receptors, for example mGluR6. The metabotropic G-protein coupled receptors are indirectly linked to ion channels in the membrane via a signal transduction cascade mediated by specific G-proteins accomplishing an amplification of the signal. That is, activated G-proteins regulate the activity of enzymes, for example adenylate cyclase, which rapidly produce large quantities of product, for example cAMP, which may in turn activate large numbers of ion channels in the cell membrane. In contrast to such metabotropic GPCRs, ionotropic receptors are directly linked to ion channels in the membrane. Therefore, ionotropic receptors like channelrhodopsin are not capable of signal amplification like metabotropic receptors.

One aspect of the invention concerns a chimeric GPCR protein, comprising domains which are derived from at least two GPCR family members:

A first of the at least two GPCR family members contributes domains which mediate the light sensitivity to the chimeric light-sensitive GPCR protein. This first member belongs to the family of light-sensitive GPCR proteins also called photopigments, and in some embodiments this light-sensitive GPCR protein is melanopsin, in particular human melanopsin.

A second of the at least two GPCR family members, namely mGluR6, contributes domains for coupling the light signal to the intracellular signalling cascade of mGluR6.

mGluR6 is a native component of the cell membrane of ON-bipolar cells in the inner retina. For the therapeutic aspects of the current invention these ON-bipolar cells are the target cells in which the light-sensitive chimeric GPCR protein will be expressed. Physiologically, the native ON-bipolar cell mGluR6 activates its intracellular signal cascade upon extracellular binding of glutamate. Thus, the ON bipolar cells naturally contain the specific intracellular components mediating the mGluR6 signaling cascade.

In the physiological light signal transduction pathway, light-activated healthy rod and cone photoreceptor cells respond to a decrease in light intensity with an increase in the level of glutamate released from their synaptic terminals, which then binds to mGluR6 on ON-bipolar cells, which in turn elicits an amplification of the light signal through the specific G-Protein coupled intracellular signaling cascade of mGluR6. In analogy to this natural pathway, the chimeric light-sensitive GPCR protein expressed in ON-bipolar cells of blind retinas transmits the light-signal to the still existing (Krizăj D et al., Vision Res. 50:2460-65, 2010) intracellular signal cascade of the mGluR6 receptor upon light activation.

Remarkably, the ON-bipolar cells, when complemented with the chimeric light-sensitive GPCR protein, directly perceive the light signal via the chimeric light-sensitive GPCR protein, bypassing the indirect glutamate signal that follows the light-stimulation of the photoreceptors. Thus, the chimeric light-sensitive GPCR protein is capable of directly coupling light activation to the mGluR6 signal cascade. In other words, light activation is independent of any functional rod or cone photoreceptor cells. Furthermore, the physiological amplification of the signal elicited by one photon is retained through the signalling cascade of the mGluR6.

The term "domain" in the context of this patent application refers to the intracellular and extracellular loops, the N- and C-termini and the transmembrane regions of a member of the GPCR protein family. The term "domain derived from" such as domain derived from mGluR6 or a domain derived from an opsin includes any domain for which the physiologically relevant corresponding part has an identical amino acid sequence or a similar amino acid sequence to the sequence of such domain in the physiological counterpart of the GPCR family member. In general, similar amino acid sequences or similar domains exhibit at least a 60% homology, preferably at least a 80% homology and most preferably at least a 90% homology. Similar domains also particularly include domains comprising relevant conserved amino acids, independent of whether a part of the remaining sequence is deviating or missing from the native counterpart or whether additional sequences are present in the chimeric protein that are not present in the native GPCR family member.

In some embodiments the chimeric protein comprises a light-activatable extracellular domain which is derived from a bi-stable photopigment, such as melanopsin but not rhodopsin for example. The advantage of bi-stable photopigments is that they are recycled after bleaching through recovery by light rather than by external cellular enzymes. The recovery rate is very fast and will sustain a high light-sensitivity even at high light intensities. With bi-stable photopigments, light bleaching and bleach recovery are increased equally at high light intensities, whereas rhodopsin, which is not bi-stable, looses its photosensitivity during illumination as more and more rhodopsins are bleached. Light bleaching in non-bi-stable photopigments such as rhodopsin can lead in the worst case to short-term blindness. The recovery rate could even be slower when a non-bi-stable photopigment such as rhodopsin is expressed in a foreign cell type, because the recovery enzymes are not necessarily available in proximity. In a healthy retina these enzymes are located in the retinal pigment epithelium.

Accordingly the choice of the domains of the first member of the chimeric GPCR, to be derived from a bi-stable photopigment renders the recovery of the chimeric GPCR after light-bleaching independent of the availability of bleach-recovery enzymes. In some embodiments the light-activatable domain of a bi-stable photoreceptor protein is selected from the opsin family, and most preferably is melanopsin and, if used in human patients, it is human melanopsin to avoid an immune reaction.

In some embodiments of the chimeric GPCR protein the first GPCR member contributes at least the domains containing the amino acid residues forming the Schiff base (linking the chromophore covalently to the GPCR), which are for melanopsin Tyrosine$^{149}$ (Y149) in TM3 and Lysine$^{321}$ (K321) in TM7, or all the domains derived from the domains which form the chromophore binding pocket in the physiological counterpart. The chromophore binding pocket refers to the binding site for the light pigment, which absorbs a photon such as for example 11-cis retinal in melanopsin (Hermann et al., Neuroscience letters, Vol. 376 p 76-80, 2004.)

In some other embodiments the chimeric GPCR protein comprises all of the extracellular domains of the first GPCR member, which are the N-terminus and the three extracellular loops (EL1, EL2, EL3) and additionally all of the seven transmembrane domains (TM1 to TM7) from the first GPCR member.

In either of these embodiments, at least one of the intracellular domains of the chimeric GPCR protein, i.e. at least one of the intracellular loops IL1, IL2, IL3 and/or the C terminus is derived from the second GPCR, which is mGluR6. In some embodiments the at least one intracellular domain derived from mGluR6 is IL3 or is IL3 and additionally at least one of the other intracellular domains, e.g. IL3 and IL2 or IL 3 and IL 2 and the C-terminus or other combinations.

Functional chimeric GPCR proteins according to the invention are light-sensitive and capable of coupling light activation to the mGluR6 signaling cascade. Depending on which photopigment is chosen as first GPCR member for the chimeric protein, either some or all transmembrane domains and extracellular domains of this photopigment are used.

The domains required for forming a chromophore pocket are necessary to render the chimeric protein light activatable, which according to current knowledge are for example TM3 to TM 7 in melanopsin and TM2 to TM 7 in channelrhodopsin.

The domains which are necessary for coupling light activation to the mGluR6 signaling cascade must be capable of binding to the G-Protein specific for the mGluR6 pathway, Galpha(o). IL3 appears to be particularly relevant for the specific binding to the G-protein of the GPCR signal cascade. Generally, the other intracellular loops and the C-terminus enhance the specificity of G-protein binding over embodiments in which some or all of IL1 and IL2 and the C-terminal domain are not derived from mGluR6.

In some embodiments the chimeric GPCR protein comprises domains which are derived from another bi-stable GPCR protein (or opsin chimeras based on a bi-stable GPCR) which is not the first and not the second member.

For minimizing potential immunogenic reactions and for optimizing the physiological coupling to the mGluR6 in some embodiments to be used for medical therapy in humans, the light-sensitive domains are derived from human GPCRs such as human melanopsin, human rhodopsin, human cone-opsin but also chimeric human opsins.

The light-sensitive chimeric GPCR protein is constructed by fusing the genetic information encoding domains of the GPCR members with the desired functionalities of light-sensitivity and coupling of the light activation to the signaling cascade of mGluR6 according to techniques known in the art. Identification of the desired domains and determination of suitable cutting and ligation sites at the N- and C-terminal ends of any particular domain are primarily based on 1) alignment of gene sequences/conserved residues and 2) computer modeling of the secondary and tertiary structure of the light-sensitive GPCR family member and mGluR6, using standard software available in the art. This approach has an inherent variability in the exact definition of the length of the individual domains and such variability is included within the scope of this invention when speaking of domains. Furthermore, at individual fusion sites between domains, there are generally a number of possibilities of splicing the domains together to yield a functional protein. And, evidently, deletion of portions of an amino acid sequence not required for function, conservative amino acid substitutions, for example interchanging hydrophobic with hydrophobic or hydrophilic with hydrophilic amino acids, and nucleotide substitutions are also within the scope of the invention. Accordingly, a considerable number of sequence variants particularly in regions of the fusion sites between adjacent domains of the chimeric GPCR proteins fall within the scope of the invention, provided that they yield functional chimeric GPCR proteins. In embodiments in which all of the transmembrane and the extracellular domains are derived from the first GPCR member and at least one or all of the intracellular domains are replaced with corresponding domains derived from mGluR6, all feasible cutting and ligation sites for exchanging IL1, IL2, IL3 and the C-terminus are within the scope of the invention.

Further aspects of the invention concern the genetic information of a light-activatable chimeric GPCR protein capable of coupling the light activation to the signaling cascade of mGluR6, vectors including viral vectors such as rAAVs comprising this genetic information, transgenic animals such as mice and zebra fish comprising this genetic information and cell culture cells comprising such genetic information or expressing light-activatable chimeric GPCR proteins capable of coupling the light activation to the signaling cascade of mGluR6, including in particular neuronal cell lines, inner retinal neuronal cell lines and bipolar cell lines in particular ON-bipolar cells.

A further aspect of the invention concerns methods of introducing the genetic information for expression of a light-activatable chimeric GPCR protein capable of coupling the light activation to the signaling cascade of mGluR6 into the eye, preferably into ON-bipolar cells. Yet a further aspect of the invention concerns methods of introducing the genetic information for expression of a light-activatable chimeric GPCR protein capable of coupling the light activation to the signaling cascade of mGluR6 into cell culture cells, in particular into neural cell lines, including retinal cell lines, inner retinal cell lines and bipolar cell lines.

A further aspect of the invention concerns gene therapeutic methods of introducing the light-sensitive chimeric GPCR protein capable of coupling light activation to the signaling cascade of mGluR6 into the eye, in particular into the vitreal or subretinal space to target retinal cells including ON-bipolar cells of both rod and cone photoreceptor cells, for improving vision in medical therapy. Such gene therapeutic methods include but are not limited to electroporation, viral transduction and chemical-based transfection. Such medical therapy in particular includes the treatment of partial or complete blindness, e.g. for the treatment of retinitis pigmentosa (RP) and macular degeneration (ARMD) as well as other forms of photoreceptor degeneration.

Yet a further aspect of the invention concerns the light-sensitive chimeric GPCR protein capable of coupling light-activation to the signaling cascade of mGluR6 or the genetic information encoding said chimeric protein and compositions comprising said protein or said genetic information as such or within vectors or cells for the purpose of medical therapy, in particular for improving vision, for the treatment of partial or complete blindness, for the treatment of retinitis pigmentosa (RP) and macular degeneration (ARMD) as well as other forms of photoreceptor degeneration.

Physiologically, the metabotropic glutamate receptor of ON-bipolar cells in the inner nuclear layer of the retina is activated by the neurotransmitter glutamate in response to retinal photoreceptor cell activity. When the photoreceptors are stimulated by light, the concentration of glutamate released onto ON-bipolar cells changes. The light-sensitive chimeric GPCR protein is a variant of the native mGluR6 protein, which is activated by light directly whereas the native mGluR6 protein is activated indirectly via glutamate after stimulation of the photoreceptor cells by changes in light. Therefore, patients suffering from photoreceptor degeneration can be treated by expressing a chimeric light-activatable protein comprising intracellular domains of mGluR6 capable of coupling the light activation to the signaling cascade of the mGluR6 in their ON-bipolar cells.

In some embodiments of the light-sensitive chimeric GPCR protein at least one or all of the intracellular components of melanopsin or another bi-stable photopigment are substituted with the intracellular components of mGluR6, resulting in a chimeric protein comprising the photoreceptor domains of melanopsin, which is able to drive existing intracellular mGluR6 signaling cascades in inner retinal neurons, in particular in ON-bipolar cells.

Due to artificial expression of a chimeric light activatable mGluR6-melanopsin protein in ON-bipolar cells, weak light signals are amplified by steering the physiological pre-existing fast enzymatic reactions regulated by native mGluR6. Also, such chimeric proteins will escape immune reactions, when extracellular domains of native photoreceptor proteins such as human melanopsin are used, because the only part accessible to the immune system will be identical to that of native human melanopsin.

An advantage of using mGluR6 as the first GPCR member is that mGluR6 is expressed only in ON-bipolar cells in the retina. Therefore, transgenically expressed chimeric mGluR6-melanopsin will efficiently couple to the mGluR6 signaling cascade in ON bipolar cells only. Moreover, the degradation and modulation of the chimeric protein (e.g. arrestin binding) will occur through pre-existing mGluR6 pathways, allowing full self-control of protein activity.

There is yet another particular effect of the expression of the chimeric light-sensitive mGluR6-melanopsin protein in ON bipolar cells to restore vision, which differs from other vision recovery methods: Visual contrast will actually be inverted; dark will appear bright and bright will appear dark. That is, neural circuits naturally activated by an increase in light intensity will be activated by a decrease in light intensity and vice versa. This in fact might have a key advantage over the prior art as outlined below:

Photoreceptors release relatively high levels of their neurotransmitter (glutamate) in the dark and less transmitter as the brightness increases. The ON-bipolar cells receive their input through mGluR6 receptors, which hyperpolarize the bipolar cells when activated (in the dark) and vice versa. If there are no photoreceptors, there is no glutamate, the ON-bipolar cells are depolarized and the surviving inner retina is effectively in an "extremely bright light" adaptive mode. In fact, the very slow degeneration of ON bipolar cells may be due to this sustained depolarization. Retinitis pigmentosa patients are not aware of the light adaptation of their retina, because the retinal output only signals spatial and temporal changes in light intensity. That is, if changes in intensity are not detected, the retina will effectively send no signal to the brain, although the retina is in the fully light adapted state.

For improving vision in patients with partial or total loss of photoreceptor cells, it is important to take into consideration that the retina is in a fully light-adapted state. This implies that the ON-bipolar cells are permanently relatively depolarized. Channelrhodopsin-2 expressed in ON-bipolar cells will only depolarize these cells further and thus the signal difference between the light-ON and the light-OFF state is relatively small. In contrast, the ON-bipolar cells expressing the chimeric light-sensitive mGluR6-GPCR protein according to the invention are hyperpolarized by light. Evidently, this increases signal difference and thus enhances output and accordingly light sensitivity.

DETAILED DESCRIPTION OF SOME EMBODIMENTS

Identification of the desired domains and determination of suitable cutting and ligation sites at the N- and C-terminal ends of any particular domain are primarily based on 1) alignment of gene sequences/conserved residues and 2) computer modeling of the secondary and tertiary structure of the light-sensitive GPCR family member and mGluR6, using for example, CLC Protein Workbench, I-TASSER, MODELLER, QUARK or SWISS-Model (Kiefer F et al., Nucleic Acids Res 37, D387-D392, 2009).

In some embodiments of the light-sensitive chimeric GPCR protein, the first GPCR member is melanopsin, in particular human or mouse melanopsin, and the second GPCR member is human or mouse mGluR6. For short, these embodiments of the chimeric light-sensitive GPCR proteins are called mGluR6-melanopsin.

Several embodiments for constructing a light-sensitive mGluR6-melanopsin are described below in more detail. The scope of the invention is not limited to these particular embodiments. In some embodiments IL2, IL3 and CT are derived from mGluR6, while the rest of the chimera is derived from melanopsin. In some other embodiments all three intracellular loops IL1 to IL3 and CT are derived from mGluR6 and all the transmembrane and extracellular domains are derived from melanopsin.

Figure 1:
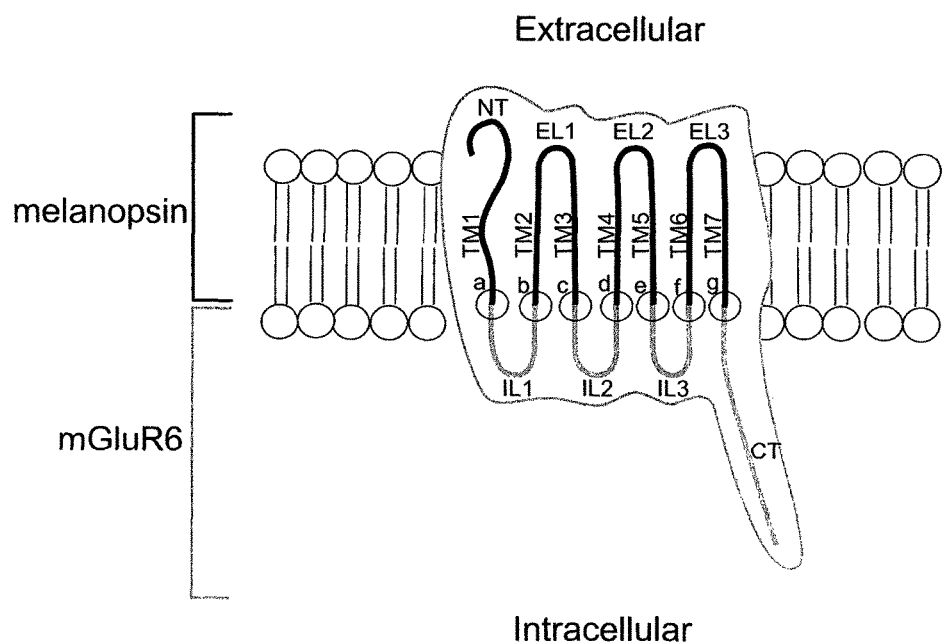
FIG. 1: Schematic drawing showing the domains and orientation across the cell membrane of an embodiment of the light-sensitive chimeric GPRC protein with the N-terminus (NT), transmembrane domains (TM1-TM7) and extracellular loops 1-3 (EL1-EL3) from melanopsin and the intracellular loops 1-3 (IL1-IL3) and the C-terminus (CT) from mGluR6.

FIG. 1 schematically shows the domains and orientation across the cell membrane of an embodiment with the N-terminus (NT), transmembrane domains (TM1-TM7) and extracellular loops 1-3 (EL1-EL3) from melanopsin and the intracellular loops 1-3 (IL1-IL3) and the C-terminus (CT) from mGluR6. Seven splicing sites are indicated with the letters a-g. In principle, all feasible cutting and ligation sites for exchanging intracellular loops of melanopsin with intracellular loops of mGluR6 are within the scope of the invention.

Table 1 discloses a number of particularly successful splicing sites for constructing mGluR6-melanopsin embodiments, which were chosen based on sequence alignment and 3D-modeling and found to be functionally active. Various combinations of alternative splicing options exist for the construction of functional mGluR6-melanopsin chimeras and are within the scope of the invention.

Tested Functional Splicing-Ligation Sites for Human mGluR6-Melanopsin:

| Site | Adjacent domains | Amino Acid Sequence at the Splicing-Ligation Site |
|---|---|---|
| a | TM 1 and IL1 | many possibilities according to the description |
| b | TM 2 and IL1 | many possibilities according to the description |
| c | TM 3 and IL2 | several tested possibilities according to the description |
| d | TM 4 and IL2 | FISPTSQVLLGVWL (SEQ ID NO: 18) |
| e | TM5 and IL 3 | 2 tested versions:<br>I) accord. to Seq. No 2: YIFIFRARGVPETF (SEQ ID NO: 19)<br>II) accord. to Seq. No. 4:<br>YIFIFRA IKA RGVPETF (SEQ ID NO: 20) |
| f | TM6 and IL 3 | ETFNEAKIMLLVIL (SEQ ID NO: 21) |
| g | TM7 and C-Terminus | IYAITHPEQNVQKR (SEQ ID NO: 22) |

For embodiments of the chimeric mGluR6-melanopsin, wherein the IL2, IL3, and C-terminal domains of melanopsin are exchanged with the corresponding domains of mGluR6 gene splicing and ligation between the transmembrane domains and the intracellular loops at sites numbered c to g according to FIG. 1 is required. The splicing sites d, e, f, g, which are indicated in Table 1, yield loop replacements which are functional as tested according to the method of Example 1. For splicing site e, two splicing versions tested are functional and listed in the table as versions I and II. While the splicing sites d, e, f, g according to Table 1 are recommended in particular, any splicing version yielding light-sensitive mGluR6-melanopsin capable of coupling light activation to the signalling cascade of mGluR6 is within the scope of the invention.

For the splicing and ligation at site c between TM 3 and IL 2 there are several options available when the amino acid sequences of melanopsin and mGluR6 are compared. Any splicing version with reasonable amino acid sequence and 3D structural homology is within the scope of the invention. It seems important to retain the DRY site between TM3 and IL2, which is the most conserved amino acid sequence in GPCR proteins. Notably, additional functional variants of the DRY site include DRIY (SEQ ID NO: 16), NRIY (SEQ ID NO: 16) or NRY. All of these variants yielded functional mGluR6-melanopsin chimeras in tests according to example 1.

For embodiments of the chimeric mGluR6-melanopsin wherein additionally IL1 of melanopsin is exchanged for IL1 of mGluR6 additional gene splicing and ligation is also required between the transmembrane domains TM1 and TM2 and the intracellular loop IL1 at sites numbered a and b according to FIG. 1. The homology between the sequences of melanopsin and mGluR6 with regards to percentage of conserved amino acids and mainly with regards to 3D structural predictions is lower in the regions of splicing and ligation sites a and b compared to sites c to g, which broadens the choice of optimal splicing and ligation sites. Preliminary tests with embodiments comprising IL1 derived from mGluR6 yielded a functional chimera and it is expected that the optimal exchange of IL1 will increase specific G-protein coupling of the chimeric protein. All feasible cutting and ligation sites for exchange of IL1 of melanopsin with IL1 of mGluR6 under consideration of their conserved amino acid sequences are within the scope of the invention.

For the following exemplary embodiments A-E of the mGluR6-melanopsin chimeric protein the entire DNA gene and amino acid sequences are listed with indication of the coding sequences corresponding to the various domains such intracellular (IL) and extracellular (EL) loops, N- and C-terminal domain (NT, CT) and transmembrane domains (TM).

A: Human mGluR6-Melanopsin Embodiment with IL2 (DRIY (SEQ ID NO: 16)), IL3 Splicing Version I and CT Derived from mGluR6

Seq. No. 1: DNA sequence
Chimera coding DNA sequence (using human genes). The underlined areas code the mGluR6 intracellular domains (IL2, IL3 (splicing version I) and CT).

| | |
|---|---|
| 1-60 | ATGAACCCTCCTTCGGGGCCAAGAGTCCCGCCCAGCCCAACCCAAGAGCCCAGCTGCATG |
| 61-120 | GCCACCCCAGCACCACCCAGCTGGTGGGACAGCTCCCAGAGCAGCATCTCCAGCCTGGGC |
| 121-180 | CGGCTTCCATCCATCAGTCCCACAGCACCTGGGACTTGGGCTGCTGCCTGGGTCCCCCTC |
| 181-240 | CCCACGGTTGATGTTCCAGACCATGCCCACTATACCCTGGGCACAGTGATCTTGCTGGTG |
| 241-300 | GGACTCACGGGGATGCTGGGCAACCTGACGGTCATCTATACCTTCTGCAGGAGCAGAAGC |
| 301-360 | CTCCGGACACCTGCCAACATGTTCATTATCAACCTCGCGGTCAGCGACTTCCTCATGTCC |
| 361-420 | TTCACCCAGGCCCCTGTCTTCTTCACCAGTAGCCTCTATAAGCAGTGGCTCTTTGGGGAG |
| 421-480 | ACAGGCTGCGAGTTCTATGCCTTCTGTGGAGCTCTCTTTGGCATTTCCTCCATGATCACC |
| 481-540 | CTGACGGCCATCGCCCTGGAC<u>CGTATCTACCGCATCTTTGAGCAGGGCAAGCGCTCGGTC</u> |
| 541-600 | <u>ACACCCCCTCCCTTCATCAGCCCCACCTCACAGGTCCTGCTGGGCGTTTGGCTCTATGCC</u> |
| 601-660 | CTGGCCTGGAGTCTGCCACCCTTCTTCGGCTGGAGCGCCTACGTGCCCGAGGGGTTGCTG |
| 661-720 | ACATCCTGCTCCTGGGACTACATGAGCTTCACGCCGG CCGTGCGTGCCTACACCATGCTT |
| 721-780 | CTCTGCTGCTTCGTGTTCTTCCTCCCTCTGCTTATCATCATCTACTGCTACATCTTCATC |
| 781-840 | TTCAGGGCC<u>CGTGGCGTGCCCGAGACCTTCAACGAGGCCAAGATCATGCTGCTGGTCATC</u> |

| | |
|---|---|
| 841-900 | CTCCTCTTCGTGCTCTCCTGGGCTCCCTATTCCGCTGTGGCCCTGGTGGCCTTTGCTGGG |
| 901-960 | TACGCACACGTCCTGACACCCTACATGAGCTCGGTGCCAGCCGTCATCGCCAAGGCCTCT |
| 961-1020 | GCAATCCACAACCCCATCATTTACGCCATCACCCACCCC<u>GAGCAGAATGTGCAGAAGCGA</u> |
| 1021-1080 | <u>AAGCGGAGCCTCAAGGCCACCTCCACGGTGGCAGCCCCACCCAAGGGCGAGGATGCAGAG</u> |
| 1081-1092 | <u>GCCCACAAGTAG</u> |

<div align="center">
Seq. No. 2: Amino acid sequence<br>
Chimeric peptide sequence (using human genes). The underlined<br>
areas code the mGluR6 intracellular domains (IL2 (<br>
[DRIY] SEQ ID NO: 16)),<br>
IL3 (splicing version I) and CT). AA in bold form ELs and<br>
framed residues Y and K are involved in chromophore binding.
</div>

| | |
|---|---|
| 1-60 | MNPPSGPRVPPSPTQEPSCMATPAPPSWWDSSQSSISSLGRLPSISPTAPGTWAAAWVPL |
| 61-120 | PTVDVPDHAHYTLGTVILLVGLTGMLGNLTVIYTFCRSRSLRTPANMFIINLAVSDFLMS |
| 121-180 | FTQAPVFFTSSLYKQWLFGETGCEH[Y]AFCGALFGISSMITLTAIALI<u>DRIY</u>RIFEQGKRSV |
| 181-240 | <u>TPPPFISPTSQ</u>VLLGVWLYALAWSLPPFFGWSAYVPEGLLTSCSWDYMSFTPAVRAYTML |
| 241-300 | LCCFVFFLPLLIIIYCYIFIFRA<u>RGVPETFNEAK</u>IMLLVILLFVLSWAPYSAVALVAFAG |
| 301-360 | YAHVLTPYMSSVPAVIA[K]ASAIHNPIIYAITHP<u>EQNVQKRKRSLKATSTVAAPPKGEDAE</u> |
| 361-363 | <u>AHK</u> |

B: Human mGluR6-Melanopsin Embodiment with IL2 (DRIY (SEQ ID NO: 16)), IL3 Splicing Version II and CT Derived from mGluR6

<div align="center">
Seq. No. 3: DNA sequence<br>
Chimera coding DNA sequence (using human genes).<br>
The underlined areas code the mGluR6 intracellular domains<br>
(IL2, IL3 (splicing version II) and CT).
</div>

| | |
|---|---|
| 1-60 | ATGAACCCTCCTTCGGGGCCAAGAGTCCCGCCCAGCCCAACCCAAGAGCCCAGCTGCATG |
| 61-120 | GCCACCCCAGCACCACCCAGCTGGTGGGACAGCTCCCAGAGCAGCATCTCCAGCCTGGGC |
| 121-180 | CGGCTTCCATCCATCAGTCCCACAGCACCTGGGACTTGGGCTGCTGCCTGGGTCCCCCTC |
| 181-240 | CCCACGGTTGATGTTCCAGACCATGCCCACTATACCCTGGGCACAGTGATCTTGCTGGTG |
| 241-300 | GGACTCACGGGGATGCTGGGCAACCTGACGGTCATCTATACCTTCTGCAGGAGCAGAAGC |
| 301-360 | CTCCGGACACCTGCCAACATGTTCATTATCAACCTCGCGGTCAGCGACTTCCTCATGTCC |
| 361-420 | TTCACCCAGGCCCCTGTCTTCTTCACCAGTAGCCTCTATAAGCAGTGGCTCTTTGGGGAG |
| 421-480 | ACAGGCTGCGAGTTCTATGCCTTCTGTGGAGCTCTCTTTGGCATTTCCTCCATGATCACC |
| 481-540 | CTGACGGCCATCGCCCTGGAC<u>CGTATCTACCGCATCTTTGAGCAGGGCAAGCGCTCGGTC</u> |
| 541-600 | <u>ACACCCCCTCCCTTCATCAGCCCCACCTCACAGG</u>TCCTGCTGGGCGTTTGGCTCTATGCC |
| 601-660 | CTGGCCTGGAGTCTGCCACCCTTCTTCGGCTGGAGCGCCTACGTGCCCGAGGGGTTGCTG |
| 661-720 | ACATCCTGCTCCTGGGACTACATGAGCTTCACGCCGGCCGTGCGTGCCTACACCATGCTT |
| 721-780 | CTCTGCTGCTTCGTGTTCTTCCTCCCTCTGCTTATCATCATCTACTGCTACATCTTCATC |
| 781-840 | TTCAGGGCCATC<u>AAGGCCCGTGGCGTGCCCGAGACCTTCAACGAGGCCAAG</u>ATCATGCTG |
| 841-900 | CTGGTCATCCTCCTCTTCGTGCTCTCCTGGGCTCCCTATTCCGCTGTGGCCCTGGTGGCC |
| 901-960 | TTTGCTGGGTACGCACACGTCCTGACACCCTACATGAGCTCGGTGCCAGCCGTCATCGCC |

| | |
|---|---|
| 961-1020 | AAGGCCTCTGCAATCCACAACCCCATCATTTACGCCATCACCCACCCC<u>GAGCAGAATGTG</u> |
| 1021-1080 | <u>CAGAAGCGAAAGCGGAGCCTCAAGGCCACCTCCACGGTGGCAGCCCCACCCAAGGGCGAG</u> |
| 1081-1101 | <u>GATGCAGAGGCCCACAAGTAG</u> |

Seq. No. 4: Amino acid sequence
Chimeric peptide sequence (using human genes). The underlined areas code the mGluR6 intracellular domains (IL2 (
<span style="border:1px solid black">DRIY</span> SEQ ID NO: 16)),
IL3 (splicing version II) and CT). AA in bold form
ELs andframed Y and K residues are involved in chromophore binding.

| | |
|---|---|
| 1-60 | MNPPSGPRVPPSPTQEPSCMATPAPPSWWDSSQSSISSLGRLPSISPTAPGTWAAAWVPL |
| 61-120 | PTVDVPDHAHYTLGTVILLVGLTGMLGNLTVIYTFCRSRSLRTPANMFIINLAVSDFLMS |
| 121-180 | FTQAPVFFTSSLYKQWLFGETGCEH<span style="border:1px solid black">Y</span>AFCGALFGISSMITLTAIAL<span style="border:1px solid black">DRIY</span>RIFEQGKRSV |
| 181-240 | TPPPFISPTSQVLLGVWLYALAWSLPPFFGWSAYVPEGLLTSCSWDYMSFTPAVRAYTML |
| 241-300 | LCCFVFFLPLLIIIYCYIFIFRAI<u>KARGVPETFNEAK</u>IMLLVILLFVLSWAPYSAVALVA |
| 301-360 | FAGYAHVLIPYMSSVPAVIA<span style="border:1px solid black">K</span>ASAIHNPIIYAITHP<u>EQNVQKRKRSLKATSTVAAPPKGE</u> |
| 361-366 | <u>DAEAHK</u> |

25

C: Human mGluR6-Melanopsin Embodiment with IL1, IL2(DRIY (SEQ ID NO: 16)), IL3 Splicing Version I and CT Derived from mGluR6

Seq. No. 5: DNA sequence
Chimera coding DNA sequence (using human genes). The underlined areas code the mGluR6 intracellular domains (IL1, IL2, IL3 (splicing version I) and CT).

| | |
|---|---|
| 1-60 | ATGAACCCTCCTTCGGGGCCAAGAGTCCCGCCCAGCCCAACCCAAGAGCCCAGCTGCATG |
| 61-120 | GCCACCCCAGCACCACCCAGCTGGTGGGACAGCTCCCAGAGCAGCATCTCCAGCCTGGGC |
| 121-180 | CGGCTTCCATCCATCAGTCCCACAGCACCTGGGACTTGGGCTGCTGCCTGGGTCCCCCTC |
| 181-240 | CCCACGGTTGATGTTCCAGACCATGCCCACTATACCCTGGGCACAGTGATCTTGCTGGTG |
| 241-300 | GGACTCACGGGGATGCTGGGCAACCTGACGGTCATCTATACCTTC<u>GTGCGGTACAACAAC</u> |
| 301-360 | <u>ACGCCCATCGTCCGGGCCTCGGGCCGAGAGCTC</u>TTCATTATCAACCTCGCGGTCAGCGAC |
| 361-420 | TTCCTCATGTCCTTCACCCAGGCCCCTGTCTTCTTCACCAGTAGCCTCTATAAGCAGTGG |
| 421-480 | CTCTTTGGGGAGACAGGCTGCGAGTTCTATGCCTTCTGTGGAGCTCTCTTTGGCATTTCC |
| 481-540 | TCCATGATCACCCTGACGGCCATCGCCCTGGAC<u>CGTATCTACCGCATCTTTGAGCAGGGC</u> |
| 541-600 | <u>AAGCGCTCGGI CACACCCCCTCCCTTCATCAGCCCCACCTCACAG</u>GTCCTGCTGGGCGTT |
| 601-660 | TGGCTCTATGCCCIGGCCTGGAGTCTGCCACCCTTCTTCGGCTGGAGCGCCTACGTGCCC |
| 661-720 | GAGGGGTTGCTGACATCCTGCTCCTGGGACTACATGAGCTTCACGCCGGCCGTGCGTGCC |
| 721-780 | TACACCATGCTTCTCTGCTGCTTCGTGTTCTTCCTCCCICTGCTTATCATCATCTACTGC |
| 781-840 | TACATCTTCATCTTCAGGGCCATC<u>AAGGCCCGTGGCGTGCCCGAGACCTTCAACGAGGCC</u> |
| 841-900 | <u>AAG</u>ATCATGCTGCTGGTCATCCTCCTCTTCGTGCTCTCCTGGGCTCCCTATTCCGCTGTG |
| 901-960 | GCCCTGGTGGCCTTTGCTGGGTACGCACACGTCCTGACACCCTACATGAGCTCGGTGCCA |
| 961-1020 | GCCGTCATCGCCAAGGCCTCTGCAATCCACAACCCCATCATTTACGCCATCACCCACCCC |
| 1021-1080 | <u>GAGCAGAATGTGCAGAAGCGAAAGCGGAGCCTCAAGGCCACCTCCACGGTGGCAGCCCCA</u> |
| 1081-1113 | <u>CCCAAGGGCGAGGATGCAGAGGCCCACAAGTAG</u> |

-continued

Seq. No. 6: Amino acid sequence
Chimeric peptide sequence (using human genes). The underlined areas
code the mGluR6 intracellular domains (IL1, IL2 (
DRIY SEQ ID NO: 16)),
IL3 (splicing version I) and CT). AA in bold form ELs and
framed Y and K residues are involved in chromophore binding.

| | |
|---|---|
| 1-60 | MNPPSGPRVPPSPTQEPSCMATPAPPSWWDSSQSSISSLGRLPSISPTAPGTWAAAWVPL |
| 61-120 | PTVDVPDHAHYTLGTVILLVGLIGMLGNLTVIYTF<u>VRYNNTPIVRASGREL</u>FIINLAVSD |
| 121-180 | FLMSFTQAPVFFTSSLYKQWLFGETGCEHY AFCGALFGISSMITLTAIAL<u>DRIY</u>RIFEQG |
| 181-240 | <u>KRSVTPPPFISPTSQ</u>VLLGVWLYALAWSLPPFFGWSAYVPEGLLTSCSWDYMSFTPAVRA |
| 241-300 | YTMLLCCFVFFLPLLIIIYCYIFIFRAI<u>KARGVPETFNEAK</u>IMLLVILLFVLSWAPYSAV |
| 301-360 | ALVAFAGYAHVLTPYMSSVPAVIA K ASAIHNPIIYAITHP<u>EQNVQKRKRSLKATSTVAAP</u> |
| 361-370 | <u>PKGEDAEAHK</u> |

D: Mouse mGluR6-Melanopsin (According to Embodiment A) with IL2(DRIY (SEQ ID NO: 16)), IL3 Splicing Version I and CT Derived from mGluR6

Seq. No. 7: DNA sequence
Chimera coding DNA sequence (using mouse genes). The underlined areas
code the mGluR6 intracellular domains (IL2, IL3
(splicing version I) and CT).

| | |
|---|---|
| 1-60 | ATGGACTCTCCTTCAGGACCAAGAGTCTTGTCAAGCTTAACTCAGGATCCCAGCTTCACA |
| 61-120 | ACCAGTCCTGCCCTGCAAGGCATTTGGAACGGCACTCAGAACGTCTCCGTAAGAGCCCAG |
| 121-180 | CTTCTCTCTGTTAGCCCCACGACATCTGCACATCAGGCTGCTGCCTGGGTCCCCTTCCCC |
| 181-240 | ACAGTCGATGTCCCAGACCATGCTCACTATACCCTAGGCACGGTGATCCTGCTGGTGGGA |
| 241-300 | CTCACAGGGATGCTGGGCAATCTGACGGTCATCTACACCTTCTGCAGGAACAGAGGCCTG |
| 301-360 | CGGACACCAGCAAACATGTTCATCATCAACCTCGCAGTCAGCGACTTCCTCATGTCAGTC |
| 361-420 | ACTCAGGCCCCGGTGTTCTTTGCCAGCAGCCTCTACAAGAAGTGGCTCTTTGGGGAGACA |
| 421-480 | GGTTGCGAGTTCTATGCCTTCTGCGGGCTGTCTTTGGCATCACTTCCATGATCACCCTG |
| 481-540 | ACAGCCATAGCCATGGAC<u>CGCATCTACCGCATTTTCGAGCAAGGGAAGCGCTCTGTCACG</u> |
| 541-600 | <u>CCGCCACCCTTCATCAGCCCCACCTCGCAG</u>GTCCTGCTAGGCGTCTGGCTTTATGCCCTG |
| 601-660 | GCCTGGAGTCTGCCACCTTTCTTTGGTTGGAGTGCCTACGTGCCCGAGGGGCTGCTGACA |
| 661-720 | TCCTGCTCCTGGGACTACATGACCTTCACACCCCAGGTGCGTGCCTACACCATGCTGCTC |
| 721-780 | TTCTGCTTTGTCTTCTTCCTCCCCCTGCTCATCATCATCTTCTGCTACATCTTCATCTTC |
| 781-840 | AGGGCC<u>CGAGGTGTGCCAGAGACCTTCAATGAAGCCAAG</u>GTCGCACTGATTGTCATTCTT |
| 841-900 | CTCTTCGTGCTGTCCTGGGCTCCCTACTCCACTGTGGCTCTGGTGGCCTTTGCTGGATAC |
| 901-960 | TCGCACATCCTGACGCCCTACATGAGCTCGGTGCCAGCCGTCATCGCCAAGGCTTCTGCC |
| 961-1020 | ATCCACAATCCCATTATCTACGCCATCACTCACCCC<u>GAGCAGAACGTGCAGAAGCGGAAG</u> |
| 1021-1080 | <u>CGCAGCCTCAAGAAGACCTCCACGATGGCGGCCCCGCCCAAGAGCGAGAACTCAGAGGAC</u> |
| 1081-1089 | <u>GCCAAGTAG</u> |

Seq. No. 8: Amino acid sequence
Chimeric peptide sequence (using mouse genes). The underlined areas code the mGluR6 intracellular domains (IL2 (DRIY), IL3 (splicing version I) and CT). AA in bold form ELs and framed Y and K residues are involved in chromophore binding.

| | |
|---|---|
| 1-60 | MDSPSGPRVLSSLTQDPSFTTSPALQGIWNGTQNVSVRAQLLSVSPTTSAHQAAAWVPFP |
| 61-120 | TVDVPDHAHYTLGTVILLVGLTGMLGNLTVIYTFCRNRGLRTPANMFIINLAVSDFLMSV |
| 121-180 | TQAPVFFASSLYKKWLFGETGCEFYAFCGAVFGITSMITLTAIAMDRIYRIFEQGKRSVT |
| 181-240 | PPPFISPTSQVLLGVWLYALAWSLPPFFGWSAYVPEGLLTSCSWDYMTFTPQVRAYTMLL |
| 241-300 | FCFVFFLPLLIIIFCYIFIFRARGVPETFNEAKVALIVILLFVLSWAPYSTVALVAFAGY |
| 301-360 | SHILTPYMSSVPAVIA K ASAIHNPIIYAITHPEQNVQKRKRSLKKTSTMAAPPKSENSED |
| 361-362 | AK |

E: Mouse mGluR6-Melanopsin (According to Embodiment C) with IL1, IL2(DRIY), IL3 Splicing Version I and CT Derived from mGluR6

Seq. No. 9: DNA sequence
Chimera coding DNA sequence (using mouse genes). The underlined areas code the mGluR6 intracellular domains (IL 1, IL2, IL3 (splicing version I) and CT).

| | |
|---|---|
| 1-60 | ATGGACTCTCCTTCAGGACCAAGAGTCTTGTCAAGCTTAACTCAGGATCCCAGCTTCACA |
| 61-120 | ACCAGTCCTGCCCTGCAAGGCATTTGGAACGGCACTCAGAACGTCTCCGTAAGAGCCCAG |
| 121-180 | CTTCTCTCTGTTAGCCCCACGACATCTGCACATCAGGCTGCTGCCTGGGTCCCCTTCCCC |
| 181-240 | ACAGTCGATGTCCCAGACCATGCTCACTATACCCTAGGCACGGTGATCCTGCTGGTGGGA |
| 241-300 | CTCACAGGGATGCTGGGCAATCTGACGGTCATCTACACCTTCATGCGACACAACGACACT |
| 301-360 | CCCATAGTCCGCGCCTCTGGCCGTGAGCTTTTCATCATCAACCTCGCAGTCAGCGACTTC |
| 361-420 | CTCATGTCAGTCACTCAGGCCCCGGTCTTCTTTGCCAGCAGCCTCTACAAGAAGTGGCTC |
| 421-480 | TTTGGGGAGACAGGTTGCGAGTTCTATGCCTTCTGCGGGGCTGTCTTTGGCATCACTTCC |
| 481-540 | ATGATCACCCTGACAGCCATAGCCATGGACCGCATCTACCGCATTTTCGAGCAAGGGAAG |
| 541-600 | CGCTCTGTCACGCCGCCACCCTTCATCAGCCCCACCTCGCAGGTCCTGCTAGGCGTCTGG |
| 601-660 | CTTTATGCCCTGGCCTGGAGTCTGCCACCTTTCTTTGGTTGGAGTGCCTACGTGCCCGAG |
| 661-720 | GGGCTGCTGACATCCTGCTCCTGGGACTACATGACCTTCACACCCCAGGTGCGTGCCTAC |
| 721-780 | ACCATGCTGCTCTTCTGCTTTGTCTTCTTCCTCCCCCTGCTCATCATCATCTTCTGCTAC |
| 781-840 | ATCTTCATCTTCAGGGCCCGAGGTGTGCCAGAGACCTTCAATGAAGCCAAGGTCGCACTG |
| 841-900 | ATTGTCATTCTTCTCTTCGTGCTGTCCTGGGCTCCCTACTCCACTGTGGCTCTGGTGGCC |
| 901-960 | TTTGCTGGATACTCGCACATCCTGACGCCCTACATGAGCTCGGTGCCAGCCGTCATCGCC |
| 961-1020 | AAGGCTTCTGCCATCCACAATCCCATTATCTACGCCATCACTCACCCCGAGCAGAACGTG |
| 1021-1080 | CAGAAGCGGAAGCGCAGCCTCAAGAAGACCTCCACGATGGCGGCCCCGCCCAAGAGCGAG |
| 1081-1101 | AACTCAGAGGACGCCAAGTAG |

-continued

Seq. No. 10: Amino acid sequence
Chimeric peptide sequence (using mouse genes). The underlined areas
code the mGluR6 intracellular domains (IL1, IL2 (DRIY), IL3
(splicing version I) and CT). AA in bold form ELs and framed
residues Y and K are involved in chromophore binding.

| 1-60 | MDSPSGPRVLSSLTQDPSFTTSPALQGIWNGTQNVSVRAQLLSVSPTTSAHQAAAWVPFP |
|---|---|
| 61-120 | TVDVPDHAHYTLGTVILLVGLTGMLGNLTVIYTFMRHNDTPIVRASGRELFIINLAVSDF |
| 121-180 | LMSVTQAPVFFASSLYKKWLFGETGCEH Y AFCGAVFGITSMITLTAIAMDRIYRIFEQGK |
| 181-240 | RSVTPPPFISPTSQVLLGVWLYALAWSLPPFFGWSAYVPEGLLTSCSWDYMTFTPQVRAY |
| 241-300 | TMLLFCFVFFLPLLIIIFCYIFIFRARGVPETFNEAKVALIVILLFVLSWAPYSTVALVA |
| 301-360 | FAGYSHILTPYMSSVPAVIA K ASAIHNPIIYAITHPEQNVQKRKRSLKKTSTMAAPPKSE |
| 361-366 | NSEDAK |

Examples documenting light activation to the signaling cascade of mGluR6 by an exemplary mGluR6 chimeric GPCR protein, in particular by an exemplary mGluR6-melanopsin chimeric protein:

In these first experiments, a functional analysis of mGluR6-Melanopsin Chimera in cultured human embryonic kidney cells (HEK293 cells) stably expressing a GIRK potassium channel is performed:

This experiment tests functional coupling of light-activation of chimera according to exemplary embodiment D (Seq. No. 7/8) to GIRK channels in HEK293 cells, a known ability of functionally activated mGluR6 and requires the expression of embodiments of the light-sensitive mGluR6-melanopsin in cultured human embryonic kidney cells (HEK293 cells) stably expressing a GIRK potassium channel (HEK293-GIRK cells).

In HEK293-GIRK cells mGluR6 couples intracellularly via a G-protein to the heteromeric Kir3.1/3.2 potassium channel (GIRK channel). Therefore, successful light-activation of the mGluR6-melanopsin chimera can be indirectly shown via activation of GIRK channels, resulting in K$^+$-currents measurable in electrophysiological experiments, as shown in FIG. 2 and FIG. 3.

Figure 2:
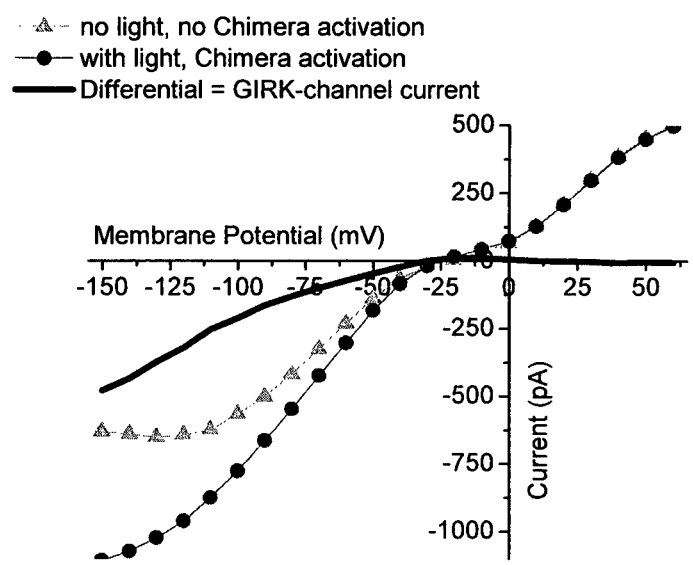
FIG. 2: Example 1 Whole cell current responses of HEK293(GIRK) cells transfected with mouse mGluR6-melanopsin (IL2(DRIY), IL3(I) and CT from mGluR6, exemplary embodiment D with Seq. No. 7/8)—presently preferred sequence with biggest currents measured in HEK293 (GIRK) cells

FIG. 2 shows whole-cell current responses to 1-s voltage ramps between −150 and +60 mV recorded from HEK293-GIRK cells transfected with chimera according to exemplary embodiment D (Seq. No. 7/8) When the mGluR6-melanopsin chimera is activated by blue (473 nm) light (dark grey trace), GIRK channels are activated. Currents were measured in the absence of light (no mGluR6-melanopsin activation, light grey triangles) and in the presence of light (with mGluR6-melanopsin activation, dark grey circles). The differential is shown as a thick black line and represents the current-voltage relationship of GIRK-channels.

Figure 3:
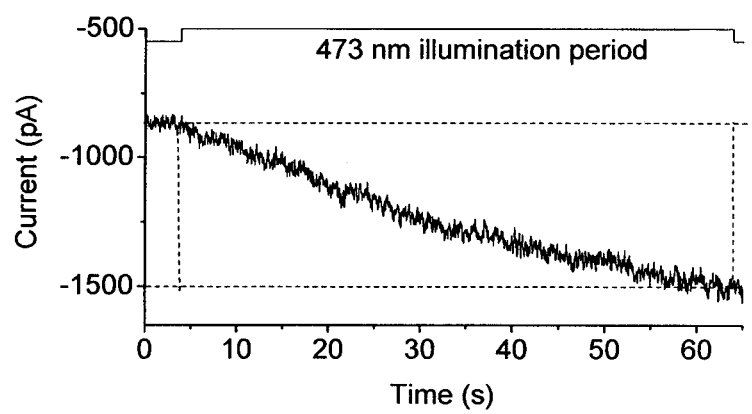
FIG. 3: Example 1: Outward $K^+$ currents

FIG. 3 shows the results of whole-cell patch clamp experiments in HEK293-GIRK cells transfected with the same embodiment of mGluR6-melanopsin chimera according to exemplary embodiment D (Seq. No. 7/8). The outward K$^+$-currents through GIRK channels become visible as hyperpolarizing currents during the 473 illumination period.

The results shown in FIG. 2 and FIG. 3 performed with mGluR6-melanopsin chimera according to exemplary embodiment D (Seq. No. 7/8) show:

The extracellular Melanopsin part of the chimera is activated by blue light and switched off when blue light is switched off.

The intracellular mGluR6 part of the chimera couples successfully via a G-protein to the GIRK potassium channels, so that an outward K$^+$-current is measured during light stimulation, which shows kinetics typical of GIRK channels.

Therefore, it is concluded that the mGluR6-melanopsin chimera is functional.

Gene therapeutic methods as they are known in the art may be applied for expression of the light-sensitive GPCR chimeric protein capable of coupling light activation to the signaling cascade of mGluR6. Below two particular methods, rAAV transduction and electroporation, are described, but the invention is not limited to these particular exemplary methods:

rAAV transduction is a first example of an applicable approach known in the art: First the sclera is carefully punctured with a hypodermic needle and then approximately 1 microliter of rAAV (corresponding to approximately 10$^{10}$ Genome copies) is subretinally (Pang J J et al. Invest Ophthalmol Vis Sci. 49(10):4278-83, 2008) or intravitreally (safer and probably more efficient—Park et al. Gene Ther 16(7): 916-926, 2009) injected into the eye. After approximately 4 weeks the chimera is expressed and electrophysiological/morphological experiments can be performed.

rAAV shuttles for gene delivery hold a number of gene therapeutic advantages:

a) rAAV2s are currently the most successful vectors for gene therapy, they display minimal immunogenicity (Buch P K et al. Gene Ther 15:849-857, 2008).

b) There exist several serotypes with different cell specificity. Capsid phenylalaline (F) for tyrosine (F) mutations of Serotype 8 {rAAV2/8 (Y733F)} and Serotype 2 {rAAV2/2 (Y252, 272, 444, 500, 704, 730F)} are currently the most promising rAAV shuttles to transduce inner retinal cells (Pang J J et al. Gen Ther 19(2):234-242, 2011; Petrs-Silva H et al., Mol Ther 19(2): 293-301, 2011).

c) rAAV delivery results in long-term DNA expression (several years or even permanently)—single rAAV-treatment is sufficient, no reapplication necessary.

d) DNA-localization to ON-bipolar cells can be achieved e.g. by:

I) rAAV serotype (rAAV2/8 and rAAV2/2 presently most promising for inner retinal cells), II) rAAV receptor targeting of specific ON-bipolar cell surface proteins (i.e. nyctalopin, mGluR6, TRPM12), III) ON-bipolar cell specific promoter or enhancer/promoter sequence (mGluR6 and mGluR6/sv40 promoters are commonly used, alternatively the promoter/enhancer sequence is derived from that of Ggamma13, that of nyctalopin or that of TRPM12), IV) the presence of the mGluR6 specific G-protein Galpha (o) exclusively in ON-bipolar cells, so only ON-bipolar cells can effectively couple mGluR6 to their enzymatic cascade.

Electroporation is a second example of an applicable approach known in the art: DNA coding for the chimeric protein under the control of an ON-bipolar cell-specific promoter are dissolved in a sterile saline solution and injected subretinally. The injection is followed by application of transretinal voltage pulses using one electrode behind the retina and one in front of the retina. The polarity of the voltages steps is positive at the ganglion cell side and negative at the photoreceptor side. The voltage pulses act to temporarily permeabilize the cell membrane, while at the same time pulling the negatively charged DNA towards the positive pole and into retinal cells (Lagali P S et al. Nat Neurosci. 11(6):667-75, 2008, Matsuda T and Cepko C L, PNAS 101(1):16-22, 2004).

The following examples document rAAV transduction and expression of DNA encoding an exemplary light-sensitive GPCR chimeric protein capable of coupling light activation to the signaling cascade specifically in mouse ON-bipolar cells, and in particular of transduction and expression of DNA encoding an exemplary mGluR6-melanopsin chimeric protein:

In a first series of experiment, it is tested if the mGluR6-melanopsin chimeric gene according to according to exemplary embodiment D (Seq. No. 8) is delivered into the ON-bipolar cells of the mouse retina using tyrosine-capsid mutated recombinant adeno-associated virus rAAV2/8 (Y733F) and rAAV2/2(Y252, 272, 444, 500, 704, 730F).

This experiment also tests if specific ON-bipolar cell expression of mGluR6-melanopsin (chimera embodiment D) is achieved using the mGluR6 enhancer sv40 basal promoter element (Kim D S et el., J Neurosci 28(31):7748-64, 2008).

Figure 4:
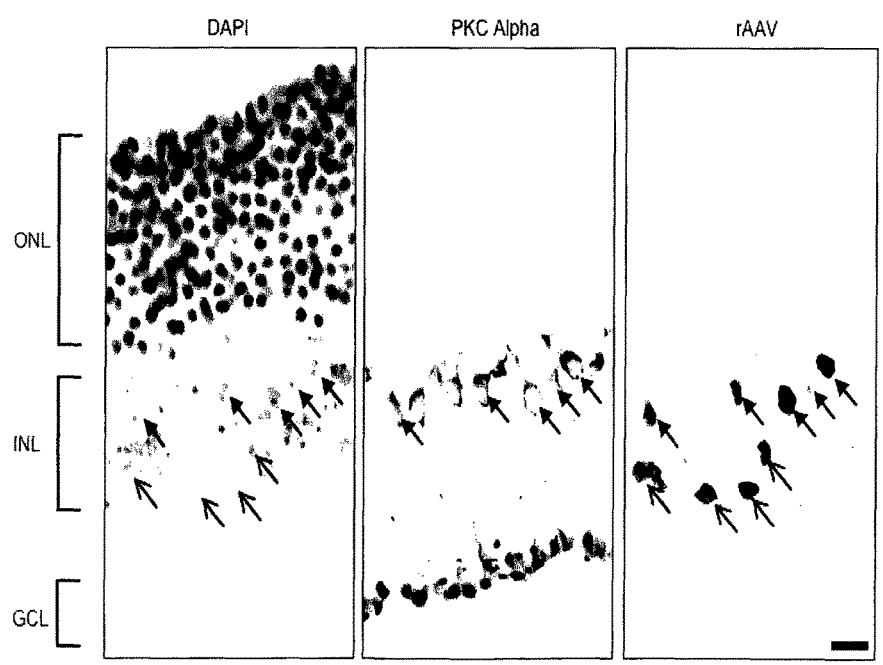
FIG. 4: Example 2: Successful and specific mGluR6-melanopsin transduction of mouse ON-bipolar cells using a rAAV2 capsid mutant vector

The results are shown in FIG. 4 and document successful and specific mGluR6-melanopsin transduction of mouse rod and cone ON-bipolar cells using a rAAV2/2 capsid mutant vector six weeks after subretinal or intravitreal administration, as detailed below:

A section through a mouse retina transduced with PRm-GluR6/sv40-"mGluR6-melanopsin"-IRES-TurboFP635 using a rAAV2/2 vector containing six capsid phenylalaline (F) for tyrosine (F) mutations (Y252, 272, 444, 500, 704, 730F; Petrs-Silva H et al., Mol Ther 19(2): 293-301, 2011). The virus was injected subretinally six weeks prior to anatomical analysis. Expression of the transgene (mGluR6-melanopsin) and the reporter (TurboFP635) was driven by the mGluR6 enhancer sv40 basal promoter element (Kim D S et el., J Neurosci 28(31):7748-64, 2008). In the first panel, nuclear staining with DAPI shows the outer nuclear layer (ONL), the inner nuclear layer (INL) and ganglion cell layer (GCL) of the retina. In the second panel, all rod ON bipolar cells were labeled using a PKC Alpha antibody. The last panel (rAAV) shows the TurboFP635 reporter gene, and therefore indicates successful transduction with the PRm-GluR6/sv40-"mGluR6-melanopsin"-IRES-TurboFP635 construct.

Five rod ON bipolar cells show reporter labeling (solid arrow heads), while four additional cells labeled within the INL likely indicate cone ON bipolar cells (open arrow heads). This is proof-of-principle that the light-activatable protein mGluR6-melanopsin can be introduced and expressed specifically in the target cells (ON bipolar cells) using rAAV vectors, which are admitted for clinical gene therapeutic treatment in the human eye (Jacobson S et al., Arch Ophthalmol 298v1-16, 2011). The scale bar indicates 10 μM.

Electrophysiological methods as they are known in the art may be applied to test the proper function of mGluR6-melanopsin expressed in retinal ON-bipolar cells of blind rd1 (Pde6b$^{rd1}$) FVB/N mice.

Therefore, in a second series of experiments, a functional analysis of the mGluR6-melanopsin chimera in the mouse retina ex vivo shows that mGluR6-melanopsin introduced into the ON-bipolar cells of the retina of a blind rd1 mouse (without photoreceptors) renders the retina light sensitive.

Figure 5:
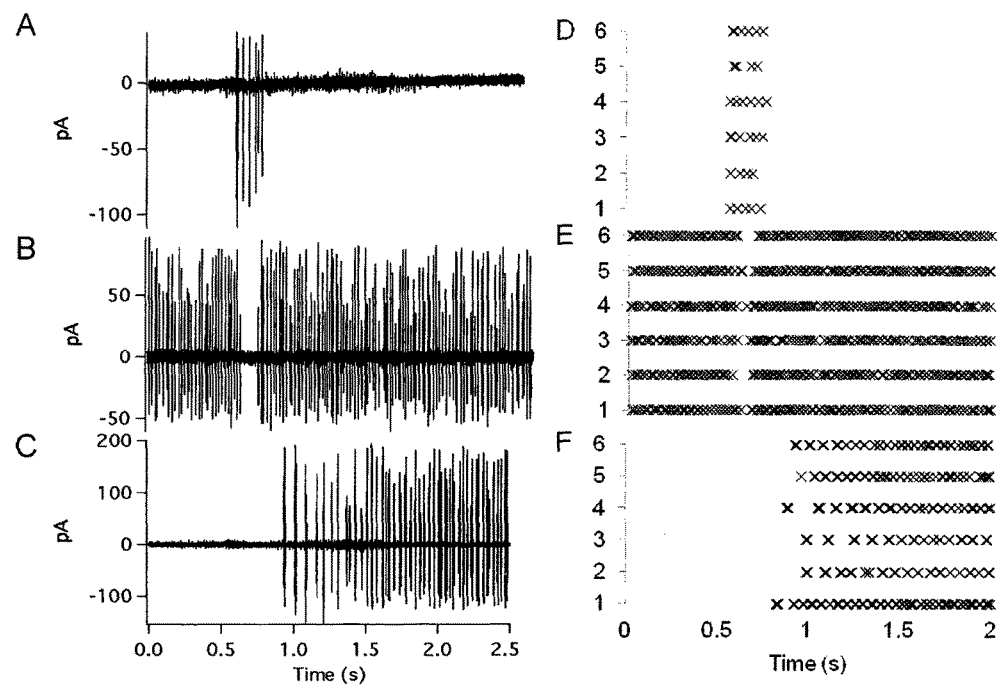
FIGS. 5A-C: Light responses recorded from three examples of retinal ganglion cells in eight week old rd1 mouse retina (retina without photoreceptor cells), one month after introducing mGluR6-melanopsin into the retinal ON bipolar cells using a rAAV2 vector. Extracellular responses from three cell types are shown, a transient ON cell (A) a transient OFF cell (B) and a sustained ON cell (C). Raster plots (D-F) are shown next to each trace.

FIG. 5 shows three examples of light responses from different types of ganglion cells in retinal whole mounts of blind rd1 mice, which have been treated with rAAVs containing the mGluR6-melanopsin (chimera embodiment D Seq. No. 7) gene:

In particular the light responses were recorded from retinal ganglion cells in nine week old rd1 mouse retina (retina without photoreceptor cells), one month after introducing mGluR6-melanopsin into the retinal ON bipolar cells using a rAAV vector as detailed below:

Extracellular responses from three cell types are shown, a transient ON cell (A) a transient OFF cell (B) and a sustained ON cell (C). Raster plots next to each trace (D-F) demonstrate that light responses to the same light stimulus were reproducible. 465-nm light was projected onto the retinal whole mounts for the duration indicated in grey below the extracellular traces.

And it is noted that, the sustained response (B) is unlikely to be that of a melanopsin ganglion cell, which are known to have a significantly slower spike onset (>2.5 sec; Schmidt T M et al., Neurophysiol 100(1):371-84, 2008) in the absence of photoreceptor input.

Thus, the results shown in FIG. 5 document that mGluR6-melanopsin expressed in ON-bipolar cells is able to restore light sensitivity in the blind retina.

In summary, FIGS. 4 and 5 show that:

rAAVs, which are admitted for clinical gene therapeutic treatment in the human eye (Jacobson S et al., Arch Ophthalmol 298v1-16, 2011), are able to deliver the mGluR6-melanopsin gene to the ON-bipolar cells.

rAAV serotype, rAAV capsid-mutations and cell-specific promoter/enhancer elements can be used to specifically target ON-bipolar cells for mGluR6-melanopsin expression.

Expressed mGluR6-melanopsin is functional and renders a blind retina light sensitive.

Therefore, it is concluded that mGluR6-melanopsin is functional in its target cells, the bipolar cells of the retina.

An optimal light-sensor for ON-bipolar cells should give a large differential light response. mGluR6-melanopsin hyperpolarizes the ON-bipolar cells upon light stimulation, as opposed to channelrhodopsin, which is depolarizing. Since ON bipolar cells in a blind rd1 mouse are already in a light-adapted (depolarized) state, mGluR6-melanopsin light activation results in a large differential light response.

Figure 6:
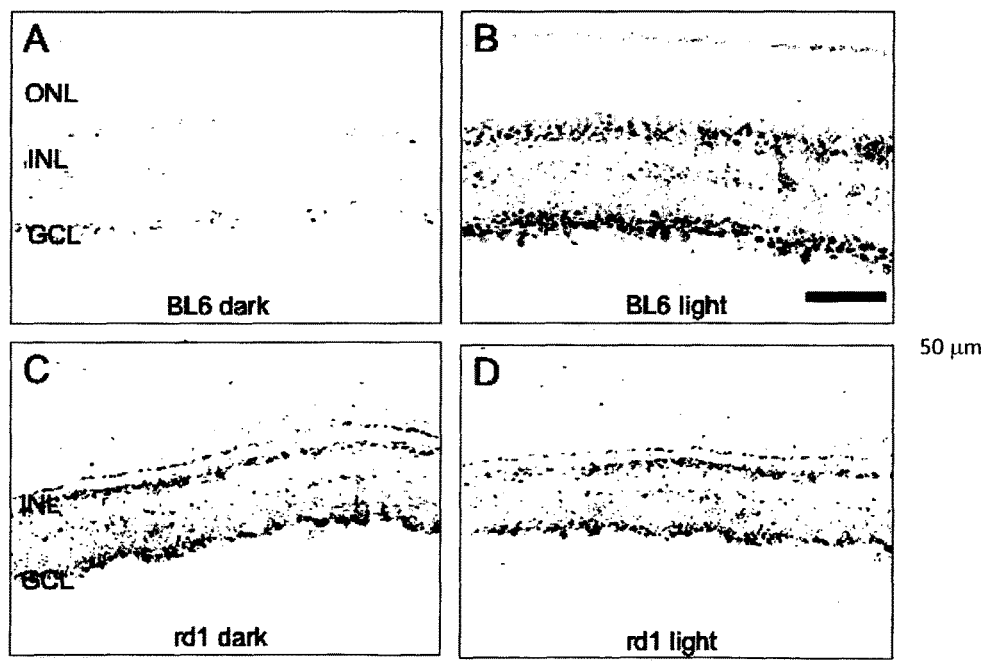
FIGS. 6A-D: Immunolabelling with the rabbit anti-Rab1A antibody: Panels A-D show sections through mouse retina of blind rd mice and wildtype mice. The immunolabeling results are shown for the dark-adapted retina of wildtype (A) and the light-adapted retina of wildtype (B) as well as dark-adapted retina of blind rd1 (C) and light-adapted retina of blind rd1 (D). This shows that the dark-adapted retina of a blind rd1 mouse is in a light-adapted, depolarized state.

FIG. 6 shows that the retina of a dark-adapted blind rd1 (Pde6b$^{rd1}$) FVB/N mouse is in a light-adapted state.

Panels A-D show sections through mouse retina of blind and wildtype mice immunolabeled with the rabbit anti-Rab1A antibody in order to show that the dark-adapted retina of a blind rd1 mouse is in fact in a "light-adapted" (depolarized) state, which corresponds to the "light-adapted" state of a wildtype retina. The anti-Rab1A antibody labels ON bipolar cells of the inner retina (inner nuclear layer (INL), terminals in ganglion cell layer (GCL)) and its expression level depends, in a healthy retina, on the ambient light intensity (Huang W et al., J Vis Neurosci 26(5-6):443-452, 2009). As expected, anti-Rab1A immunolabeling (black structures) was only visible in the light-adapted (B) and not in the dark-adapted (A) wildtype (BL6) mouse retina. However, anti-Rab1A expression levels were identical in dark—(C) and light-adapted (D) rd1 retinas, missing the outer nuclear layer (ONL) containing the photoreceptors, and anti-Rab1A expression levels were similar to the light-adapted healthy BL6 retina.

Thus, it is concluded that the rd1 retina of a blind mouse is permanently in a light-adapted (depolarized) state. The optimal light sensor should therefore hyperpolarize the ON bipolar cells upon light stimulation to guarantee a large differential light-signal, and so does mGluR6-melanopsin. Imaging exposure times of all panels were identical.

What is claimed is:

1. A chimeric G-protein-coupled-receptor (GPCR) protein comprising an N-terminal domain, a C-terminal domain, transmembrane domains, extracellular loops and intracellular loops, wherein the chimeric GPCR protein includes domains from at least two different GPCR proteins and has the domains arranged to form a GPCR protein, and wherein:
    (a) a first portion of the chimeric GPCR protein comprises transmembrane domains contributed by a first member of the G-protein-coupled-receptor (GPCR) superfamily, wherein said first member is a bi-stable opsin, wherein said transmembrane domains mediate light activation and comprise an amino acid residue that forms a Schiff base with a chromophore to covalently bind the chromophore to the GPCR protein; and
    (b) a second portion of the chimeric GPCR protein comprises one or more intracellular domains of mGluR6 selected from the intracellular loops IL1, IL2, IL3 and the C-terminal domain (CT), said second portion of the chimeric GPCR protein binding a Galpha (o) protein of the signaling cascade of mGluR6, wherein said one or more selected intracellular loops are present in the chimeric GPCR in corresponding numerically defined positions as in the native mGluR6 structure, and wherein the second portion comprises intracellular loop 3 (IL3) of mGluR6.

2. The chimeric protein of claim 1, wherein the second portion comprises intracellular loops 2 (IL2) and 3 (IL3) and the C-terminal domain of mGluR6.

3. The chimeric protein of claim 2, wherein the first portion comprises all of the domains forming a chromophore-binding pocket in the bi-stable opsin.

4. The chimeric protein of claim 3, wherein the first portion comprises transmembrane domains TM3 to TM7 of the bi-stable opsin.

5. The chimeric protein of claim 1, wherein the first portion comprises transmembrane domains TM3 to TM7, extracellular loops 1 to 3 (EL1, EL2, EL3) and the extracellular N-terminus of the bi-stable opsin; and the second portion comprises at least IL3 and the C-terminal domain of mGluR6.

6. The chimeric protein of claim 1, wherein the first portion comprises the transmembrane domains TM1 to TM7, extracellular loops 1 to 3 (EL1, EL2, EL3) and an extracellular N-terminus of the bi-stable opsin.

7. The chimeric protein of claim 6, wherein the first portion further comprises at least one but not all of the intracellular loops of the bi-stable opsin, and wherein the intracellular loops of the bi-stable opsin are present in the chimeric GPCR in the same numerical positions as in native first member of the GPCR superfamily.

8. The chimeric protein of claim 1, wherein the protein comprises SEQ ID NO: 2, SEQ ID NO: 4, SEQ ID NO: 6, SEQ ID NO: 8 or SEQ ID NO: 10, or comprises a variant of SEQ ID NO: 2, SEQ ID NO: 4, SEQ ID NO: 6, SEQ ID NO: 8, or SEQ ID NO: 10, said variant having only conservative amino acid substitutions.

9. The chimeric protein claim 1, wherein the protein is SEQ ID NO: 2 or is a variant of SEQ ID NO: 2 having only conservative amino acid substitutions.

10. The chimeric protein of claim 1, wherein the first member of the GPCR superfamily is human melanopsin.

11. The chimeric protein of claim 1, wherein the first portion comprises all the domains forming a chromophore pocket in the bi-stable opsin.

12. The chimeric protein of claim 1, wherein the second portion further comprises IL2 of mGluR6 or IL2 and the C-terminus of mGluR6.

13. A chimeric G-protein-coupled-receptor (GPCR) protein comprising an N-terminal domain, a C-terminal domain, transmembrane domains, extracellular loops and intracellular loops, wherein the chimeric GPCR protein includes domains from at least two different GPCR proteins and has the domains arranged to form a GPCR protein, and wherein:
    (a) a first portion of the chimeric GPCR protein transmembrane domains contributed by a first member of the G-protein-coupled-receptor (GPCR) superfamily, wherein said first member is a bi-stable opsin, wherein said transmembrane domains mediate light activation and comprise a lysine residue that form its a Schiff base with a chromophore to covalently bind the chromophore to the GPCR protein; and
    (b) a second portion of the chimeric GPCR protein comprises one or more intracellular domains of mGluR6 selected from the intracellular loops IL1, IL2, IL3 and the C-terminal domain (CT), said second portion of the chimeric GPCR protein binding a Galpha (o) protein of the signaling cascade of mGluR6, wherein said one or more selected intracellular loops are present in the chimeric GPCR in corresponding numerically defined positions as in the native mGluR6 structure, with the proviso that the second portion comprises at least IL3 of mGluR6.

14. The chimeric protein of claim 1, comprising 7 transmembrane domains, 3 extracellular loops, and 3 intracellular loops.

15. The chimeric protein of claim 1, wherein transmembrane domains TM3 to TM7 of the bi-stable opsin are contributed to the first portion of the chimeric GPCR protein.

16. The chimeric protein of claim 1, wherein transmembrane domains TM2 to TM7 of the bi-stable opsin are contributed to the first portion of the chimeric GPCR protein.

17. The chimeric protein of claim 1, wherein transmembrane domains TM1 to TM7 of the bi-stable opsin are contributed to the first portion of the chimeric GPCR protein.

18. The chimeric protein of claim 1, wherein the second portion comprises two intracellular domains of mGluR6 selected from the intracellular loops IL1, IL2, IL3 and the C-terminal domain (CT).

19. A method for improvement of vision in an individual comprising the steps of introducing a nucleic acid encoding a chimeric GPCR protein into the eye of the individual, wherein the chimeric GPCR protein comprises an N-terminal domain, a C-terminal domain, transmembrane domains, extracellular loops and intracellular loops, wherein the chimeric GPCR protein includes domains is derived from at least two different GPCR proteins and has the domains arranged to form a GPCR protein, and wherein:
    (a) a first portion of the chimeric GPCR protein comprises transmembrane domains contributed by a first member of the G-protein-coupled-receptor (GPCR) superfamily, wherein said first member is a bi-stable opsin, wherein said transmembrane domains mediate light activation and comprise amino acid residues that form a Schiff base which covalently binds a chromophore; and
    (b) a second portion of the chimeric GPCR protein comprises one or more intracellular domains of mGluR6 selected from the intracellular loops IL1, IL2, IL3 and the C-terminal domain (CT), said second portion of the chimeric GPCR protein binding a Galpha (o) protein of the signaling cascade of mGluR6, wherein said one or more selected intracellular loops are present in the chimeric GPCR in corresponding numerically defined positions as in the native mGluR6 structure, and wherein the second portion comprises intracellular loop 3 (IL3) of mGluR6.

20. The method of claim 19, wherein the nucleic acid is introduced into the vitreal or subretinal space of the eye.

21. The method of claim 19, wherein the individual is a human in need of treatment for partial or complete blindness, retinitis pigmentosa (RP), or macular degeneration.

22. The method of claim 19, wherein the protein comprises SEQ ID NO: 2, SEQ ID NO: 4, SEQ ID NO: 6, SEQ ID NO: 8 or SEQ ID NO: 10 or comprises a variant of one of SEQ ID NO: 2, SEQ ID NO: 4, SEQ ID NO: 6, SEQ ID NO: 8, or SEQ ID NO: 10, said variant having only conservative amino acid substitutions.

23. The method of claim 19, wherein the protein is SEQ ID NO: 2 or is a variant of SEQ ID NO: 2 having only conservative amino acid substitutions.

\* \* \* \* \*

UNITED STATES PATENT AND TRADEMARK OFFICE
CERTIFICATE OF CORRECTION

PATENT NO. : 10,112,984 B2
APPLICATION NO. : 14/128155
DATED : October 30, 2018
INVENTOR(S) : Van Wyk et al.

Page 1 of 1

It is certified that error appears in the above-identified patent and that said Letters Patent is hereby corrected as shown below:

In the Claims

Column 44, Claim 13, Lines 15-17 should read: -- and comprise a lysine residue that forms a Schiff' base with a chromophore to covalently bind the chromophore to the GPCR protein; and --

Column 44, Claim 19, Lines 53-56 should read: -- extracellular loops and intracellular loops, wherein the chimeric GPCR protein includes domains from at least two different GPCR proteins and has the domains arranged to form a GPCR protein, and wherein: --

Signed and Sealed this
Twenty-sixth Day of February, 2019

Andrei Iancu
*Director of the United States Patent and Trademark Office*

SEQUENCE LISTING

```
<160> NUMBER OF SEQ ID NOS: 22

<210> SEQ ID NO 1
<211> LENGTH: 1092
<212> TYPE: DNA
<213> ORGANISM: Homo sapiens

<400> SEQUENCE: 1
atgaaccctc cttcggggcc aagagtcccg cccagcccaa cccaagagcc cagctgcatg     60
gccaccccag caccacccag ctggtgggac agctcccaga gcagcatctc cagcctgggc    120
cggcttccat ccatcagtcc cacagcacct gggacttggg ctgctgcctg gtcccccctc    180
cccacggttg atgttccaga ccatgcccac tataccctgg gcacagtgat cttgctggtg    240
ggactcacgg ggatgctggg caacctgacg gtcatctata ccttctgcag gagcagaagc    300
ctccggacac ctgccaacat gttcattatc aacctcgcgg tcagcgactt cctcatgtcc    360
ttcacccagg cccctgtctt cttcaccagt agcctctata agcagtggct ctttggggag    420
acaggctgcg agttctatgc cttctgtgga gctctctttg gcatttcctc catgatcacc    480
ctgacggcca tcgccctgga ccgtatctac cgcatctttg agcagggcaa gcgctcggtc    540 acacccctc ccttcatcag ccccacctca caggtcctgc tgggcgtttg gctctatgcc    600
ctggcctgga gtctgccacc cttcttcggc tggagcgcct acgtgcccga ggggttgctg    660
acatcctgct cctgggacta catgagcttc acgccggccg tgcgtgccta caccatgctt    720
ctctgctgct tcgtgttctt cctccctctg cttatcatca tctactgcta catcttcatc    780
ttcaggggcc gtggcgtgcc cgagaccttc aacgaggcca agatcatgct gctggtcatc    840
ctcctcttcg tgctctcctg ggctccctat tccgctgtgg ccctggtggc ctttgctggg    900
tacgcacacg tcctgacacc ctacatgagc tcggtgccag ccgtcatcgc caaggcctct    960
gcaatccaca cccccatcat ttacgccatc acccaccccg agcagaatgt gcagaagcga   1020
aagcggagcc tcaaggccac ctccacggtg gcagccccac ccaagggcga ggatgcagag   1080
gcccacaagt ag                                                        1092

<210> SEQ ID NO 2
<211> LENGTH: 363
<212> TYPE: PRT
<213> ORGANISM: Homo sapiens

<400> SEQUENCE: 2

Met Asn Pro Pro Ser Gly Pro Arg Val Pro Pro Ser Pro Thr Gln Glu
1               5                   10                  15

Pro Ser Cys Met Ala Thr Pro Ala Pro Pro Ser Trp Trp Asp Ser Ser
            20                  25                  30

Gln Ser Ser Ile Ser Ser Leu Gly Arg Leu Pro Ser Ile Ser Pro Thr
        35                  40                  45
```

```
Ala Pro Gly Thr Trp Ala Ala Trp Val Pro Leu Pro Thr Val Asp
     50                  55                  60
Val Pro Asp His Ala His Tyr Thr Leu Gly Thr Val Ile Leu Val
 65                  70                  75                  80
Gly Leu Thr Gly Met Leu Gly Asn Leu Thr Val Ile Tyr Thr Phe Cys
                 85                  90                  95
Arg Ser Arg Ser Leu Arg Thr Pro Ala Asn Met Phe Ile Ile Asn Leu
                100                 105                 110
Ala Val Ser Asp Phe Leu Met Ser Phe Thr Gln Ala Pro Val Phe Phe
                115                 120                 125
Thr Ser Ser Leu Tyr Lys Gln Trp Leu Phe Gly Glu Thr Gly Cys Glu
130                 135                 140
Phe Tyr Ala Phe Cys Gly Ala Leu Phe Gly Ile Ser Ser Met Ile Thr
145                 150                 155                 160
Leu Thr Ala Ile Ala Leu Asp Arg Ile Tyr Arg Ile Phe Glu Gln Gly
                165                 170                 175
Lys Arg Ser Val Thr Pro Pro Phe Ile Ser Pro Thr Ser Gln Val
                180                 185                 190
Leu Leu Gly Val Trp Leu Tyr Ala Leu Ala Trp Ser Leu Pro Pro Phe
                195                 200                 205
Phe Gly Trp Ser Ala Tyr Val Pro Glu Gly Leu Leu Thr Ser Cys Ser
210                 215                 220
Trp Asp Tyr Met Ser Phe Thr Pro Ala Val Arg Ala Tyr Thr Met Leu
225                 230                 235                 240
Leu Cys Cys Phe Val Phe Phe Leu Pro Leu Leu Ile Ile Ile Tyr Cys
                245                 250                 255
Tyr Ile Phe Ile Phe Arg Ala Arg Gly Val Pro Glu Thr Phe Asn Glu
                260                 265                 270
Ala Lys Ile Met Leu Leu Val Ile Leu Leu Phe Val Leu Ser Trp Ala
                275                 280                 285
Pro Tyr Ser Ala Val Ala Leu Val Ala Phe Ala Gly Tyr Ala His Val
                290                 295                 300
Leu Thr Pro Tyr Met Ser Ser Val Pro Ala Val Ile Ala Lys Ala Ser
305                 310                 315                 320
Ala Ile His Asn Pro Ile Ile Tyr Ala Ile Thr His Pro Glu Gln Asn
                325                 330                 335
Val Gln Lys Arg Lys Arg Ser Leu Lys Ala Thr Ser Thr Val Ala Ala
                340                 345                 350
Pro Pro Lys Gly Glu Asp Ala Glu Ala His Lys
                355                 360

<210> SEQ ID NO 3
<211> LENGTH: 1101
<212> TYPE: DNA
<213> ORGANISM: Homo sapiens

<400> SEQUENCE: 3
atgaaccctc cttcggggcc aagagtcccg cccagcccaa cccaagagcc cagctgcatg      60
gccaccccag caccacccag ctggtgggac agctcccaga gcagcatctc cagcctgggc     120
cggcttccat ccatcagtcc cacagcacct gggacttggg ctgctgcctg gtcccccctc     180
cccacggttg atgttccaga ccatgcccac tataccctgg gcacagtgat cttgctggtg     240
ggactcacgg gcatgctggg caacctgacg gtcatctata ccttctgcag gagcagaagc     300
ctccggacac tgccaacat gttcattatc aacctcgcgg tcagcgactt cctcatgtcc     360
```

```
ttcacccagg cccctgtctt cttcaccagt agcctctata agcagtggct ctttggggag        420
acaggctgcg agttctatgc cttctgtgga gctctctttg gcatttcctc catgatcacc        480
ctgacggcca tcgccctgga ccgtatctac cgcatctttg agcagggcaa gcgctcggtc        540 acccccctc ccttcatcag ccccacctca caggtcctgc tgggcgtttg gctctatgcc         600
ctggcctgga gtctgccacc cttcttcggc tggagcgcct acgtgcccga ggggttgctg        660
acatcctgct cctgggacta catgagcttc acgccggccg tgcgtgccta ccatgctt         720 ctctgctgct tcgtgttctt cctccctctg cttatcatca tctactgcta catcttcatc       780
ttcagggcca tcaaggcccg tggcgtgccc gagaccttca cgaggccaa gatcatgctg        840 ctggtcatcc tcctcttcgt gctctcctgg gctccctatt ccgctgtggc cctggtggcc       900
tttgctgggt acgcacacgt cctgacaccc tacatgagct cggtgccagc cgtcatcgcc       960
aaggcctctg caatccacaa ccccatcatt tacgccatca cccaccccga gcagaatgtg      1020
cagaagcgaa agcggagcct caaggccacc tccacggtgg cagccccacc caagggcgag      1080
gatgcagagg cccacaagta g                                                 1101

<210> SEQ ID NO 4
<211> LENGTH: 366
<212> TYPE: PRT
<213> ORGANISM: Homo sapiens

<400> SEQUENCE: 4

Met Asn Pro Pro Ser Gly Pro Arg Val Pro Ser Pro Thr Gln Glu
1               5                   10                  15

Pro Ser Cys Met Ala Thr Pro Ala Pro Pro Ser Trp Trp Asp Ser Ser
                20                  25                  30

Gln Ser Ser Ile Ser Ser Leu Gly Arg Leu Pro Ser Ile Ser Pro Thr
            35                  40                  45

Ala Pro Gly Thr Trp Ala Ala Ala Trp Val Pro Leu Pro Thr Val Asp
        50                  55                  60

Val Pro Asp His Ala His Tyr Thr Leu Gly Thr Val Ile Leu Leu Val
65                  70                  75                  80

Gly Leu Thr Gly Met Leu Gly Asn Leu Thr Val Ile Tyr Thr Phe Cys
                85                  90                  95

Arg Ser Arg Ser Leu Arg Thr Pro Ala Asn Met Phe Ile Ile Asn Leu
                100                 105                 110

Ala Val Ser Asp Phe Leu Met Ser Phe Thr Gln Ala Pro Val Phe Phe
            115                 120                 125

Thr Ser Ser Leu Tyr Lys Gln Trp Leu Phe Gly Glu Thr Gly Cys Glu
        130                 135                 140

Phe Tyr Ala Phe Cys Gly Ala Leu Phe Gly Ile Ser Ser Met Ile Thr
145                 150                 155                 160

Leu Thr Ala Ile Ala Leu Asp Arg Ile Tyr Arg Ile Phe Glu Gln Gly
                165                 170                 175

Lys Arg Ser Val Thr Pro Pro Phe Ile Ser Pro Thr Ser Gln Val
                180                 185                 190

Leu Leu Gly Val Trp Leu Tyr Ala Leu Ala Trp Ser Leu Pro Pro Phe
            195                 200                 205

Phe Gly Trp Ser Ala Tyr Val Pro Glu Gly Leu Leu Thr Ser Cys Ser
        210                 215                 220

Trp Asp Tyr Met Ser Phe Thr Pro Ala Val Arg Ala Tyr Thr Met Leu
225                 230                 235                 240
```

Leu Cys Cys Phe Val Phe Phe Leu Pro Leu Leu Ile Ile Ile Tyr Cys
                245                 250                 255

Tyr Ile Phe Ile Phe Arg Ala Ile Lys Ala Arg Gly Val Pro Glu Thr
            260                 265                 270

Phe Asn Glu Ala Lys Ile Met Leu Leu Val Ile Leu Leu Phe Val Leu
        275                 280                 285

Ser Trp Ala Pro Tyr Ser Ala Val Ala Leu Val Ala Phe Ala Gly Tyr
    290                 295                 300

Ala His Val Leu Thr Pro Tyr Met Ser Ser Val Pro Ala Val Ile Ala
305                 310                 315                 320

Lys Ala Ser Ala Ile His Asn Pro Ile Ile Tyr Ala Ile Thr His Pro
                325                 330                 335

Glu Gln Asn Val Gln Lys Arg Lys Arg Ser Leu Lys Ala Thr Ser Thr
            340                 345                 350

Val Ala Ala Pro Pro Lys Gly Glu Asp Ala Glu Ala His Lys
        355                 360                 365

<210> SEQ ID NO 5
<211> LENGTH: 1113
<212> TYPE: DNA
<213> ORGANISM: Homo sapiens

<400> SEQUENCE: 5
atgaaccctc cttcggggcc aagagtcccg cccagcccaa cccaagagcc cagctgcatg      60
gccaccccag caccacccag ctggtgggac agctcccaga gcagcatctc cagcctgggc     120
cggcttccat ccatcagtcc cacagcacct gggacttggg ctgctgcctg gtcccccctc     180
cccacggttg atgttccaga ccatgccac tatacccctgg gcacagtgat cttgctggtg     240
ggactcacgg ggatgctggg caacctgacg gtcatctata ccttcgtgcg gtacaacaac     300
acgcccatcg tccgggcctc gggccgagag ctcttcatta tcaacctcgc ggtcagcgac     360
ttcctcatgt ccttcaccca ggcccctgtc ttcttcacca gtagcctcta taagcagtgg     420
ctctttgggg agacaggctg cgagttctat gccttctgtg gagctctctt tggcatttcc     480
tccatgatca ccctgacggc catcgccctg gaccgtatct accgcatctt tgagcagggc     540
aagcgctcgg tcacaccccc tcccttcatc agcccacct cacaggtcct gctgggcgtt     600
tggctctatg ccctggcctg gagtctgcca cccttcttcg gctggagcgc ctacgtgccc     660
gaggggttgc tgacatcctg ctcctgggac tacatgagct tcacgccggc cgtgcgtgcc     720
tacaccatgc ttctctgctg cttcgtgttc ttcctccctc tgcttatcat catctactgc     780
tacatcttca tcttcagggc catcaaggcc cgtggcgtgc ccgagacctt aacgaggcc     840 aagatcatgc tgctggtcat cctcctcttc gtgctctcct gggctcccta ttccgctgtg     900
gccctggtgg cctttgctgg gtacgcacac gtcctgacac cctacatgag ctcggtgcca     960
gccgtcatcg ccaaggcctc tgcaatccac aaccccatca tttacgccat cacccacccc    1020
gagcagaatg tgcagaagcg aaagcggagc ctcaaggcca cctccacggt ggcagcccca    1080
cccaagggcg aggatgcaga ggcccacaag tag                                  1113

<210> SEQ ID NO 6
<211> LENGTH: 370
<212> TYPE: PRT
<213> ORGANISM: Homo sapiens

<400> SEQUENCE: 6

```
Met Asn Pro Pro Ser Gly Pro Arg Val Pro Ser Pro Thr Gln Glu
1               5                   10                  15

Pro Ser Cys Met Ala Thr Pro Ala Pro Ser Trp Trp Asp Ser Ser
            20                  25                  30

Gln Ser Ser Ile Ser Ser Leu Gly Arg Leu Pro Ser Ile Ser Pro Thr
        35                  40                  45

Ala Pro Gly Thr Trp Ala Ala Trp Val Pro Leu Pro Thr Val Asp
    50                  55                  60

Val Pro Asp His Ala His Tyr Thr Leu Gly Thr Val Ile Leu Leu Val
65                  70                  75                  80

Gly Leu Thr Gly Met Leu Gly Asn Leu Thr Val Ile Tyr Thr Phe Val
                85                  90                  95

Arg Tyr Asn Asn Thr Pro Ile Val Arg Ala Ser Gly Arg Glu Leu Phe
            100                 105                 110

Ile Ile Asn Leu Ala Val Ser Asp Phe Leu Met Ser Phe Thr Gln Ala
            115                 120                 125

Pro Val Phe Phe Thr Ser Ser Leu Tyr Lys Gln Trp Leu Phe Gly Glu
    130                 135                 140

Thr Gly Cys Glu Phe Tyr Ala Phe Cys Gly Ala Leu Phe Gly Ile Ser
145                 150                 155                 160

Ser Met Ile Thr Leu Thr Ala Ile Ala Leu Asp Arg Ile Tyr Arg Ile
                165                 170                 175

Phe Glu Gln Gly Lys Arg Ser Val Thr Pro Pro Pro Phe Ile Ser Pro
            180                 185                 190

Thr Ser Gln Val Leu Leu Gly Val Trp Leu Tyr Ala Leu Ala Trp Ser
            195                 200                 205

Leu Pro Pro Phe Phe Gly Trp Ser Ala Tyr Val Pro Glu Gly Leu Leu
    210                 215                 220

Thr Ser Cys Ser Trp Asp Tyr Met Ser Phe Thr Pro Ala Val Arg Ala
225                 230                 235                 240

Tyr Thr Met Leu Leu Cys Cys Phe Val Phe Leu Pro Leu Leu Ile
                245                 250                 255

Ile Ile Tyr Cys Tyr Ile Phe Ile Phe Arg Ala Ile Lys Ala Arg Gly
            260                 265                 270

Val Pro Glu Thr Phe Asn Glu Ala Lys Ile Met Leu Leu Val Ile Leu
    275                 280                 285

Leu Phe Val Leu Ser Trp Ala Pro Tyr Ser Ala Val Ala Leu Val Ala
    290                 295                 300

Phe Ala Gly Tyr Ala His Val Leu Thr Pro Tyr Met Ser Ser Val Pro
305                 310                 315                 320

Ala Val Ile Ala Lys Ala Ser Ala Ile His Asn Pro Ile Ile Tyr Ala
                325                 330                 335

Ile Thr His Pro Glu Gln Asn Val Gln Lys Arg Lys Arg Ser Leu Lys
            340                 345                 350

Ala Thr Ser Thr Val Ala Ala Pro Pro Lys Gly Glu Asp Ala Glu Ala
            355                 360                 365

His Lys
    370

<210> SEQ ID NO 7
<211> LENGTH: 1089
<212> TYPE: DNA
<213> ORGANISM: Mus sp.
<220> FEATURE:
<223> OTHER INFORMATION: Mus sp.
```

<400> SEQUENCE: 7

```
atggactctc cttcaggacc aagagtcttg tcaagcttaa ctcaggatcc cagcttcaca      60
accagtcctg ccctgcaagg catttggaac ggcactcaga acgtctccgt aagagcccag    120
cttctctctg ttagccccac gacatctgca catcaggctg ctgcctgggt ccccttcccc    180
acagtcgatg tcccagacca tgctcactat accctaggca cggtgatcct gctggtggga    240
ctcacaggga tgctgggcaa tctgacggtc atctacacct tctgcaggaa cagaggcctg    300
cggacaccag caaacatgtt catcatcaac ctcgcagtca gcgacttcct catgtcagtc    360
actcaggccc cggtcttctt tgccagcagc ctctacaaga gtggctcttt ggggagaca    420
ggttgcgagt ctatgccttt ctgcggggct gtctttggca tcacttccat gatcaccctg    480
acagccatag ccatggaccg catctaccgc attttcgagc aagggaagcg ctctgtcacg    540
ccgccaccct tcatcagccc cacctcgcag gtcctgctag gcgtctggct ttatgccctg    600
gcctggagtc tgccaccttt ctttggttgg agtgcctacg tgcccgaggg gctgctgaca    660
tcctgctcct gggactacat gaccttcaca ccccaggtgc gtgcctacac catgctgctc    720
ttctgctttg tcttcttcct cccctgctc atcatcatct tctgctacat cttcatcttc    780
agggcccgag gtgtgccaga gaccttcaat gaagccaagg tcgcactgat tgtcattctt    840
ctcttcgtgc tgtcctgggc tccctactcc actgtggctc tggtggcctt tgctggatac    900
tcgcacatcc tgacgcccta catgagctcg gtgccagccg tcatcgccaa ggcttctgcc    960
atccacaatc ccattatcta cgccatcact caccccgagc agaacgtgca gaagcggaag   1020
cgcagcctca gaagaccctc cacgatggcg gccccgccca gagcgagaaa ctcagaggac   1080
gccaagtag                                                           1089
```

<210> SEQ ID NO 8
<211> LENGTH: 362
<212> TYPE: PRT
<213> ORGANISM: Mus sp.

<400> SEQUENCE: 8

```
Met Asp Ser Pro Ser Gly Pro Arg Val Leu Ser Leu Thr Gln Asp
1               5                   10                  15

Pro Ser Phe Thr Thr Ser Pro Ala Leu Gln Gly Ile Trp Asn Gly Thr
                20                  25                  30

Gln Asn Val Ser Val Arg Ala Gln Leu Leu Ser Val Ser Pro Thr Thr
            35                  40                  45

Ser Ala His Gln Ala Ala Ala Trp Val Pro Phe Pro Thr Val Asp Val
        50                  55                  60

Pro Asp His Ala His Tyr Thr Leu Gly Thr Val Ile Leu Leu Val Gly
    65                  70                  75                  80

Leu Thr Gly Met Leu Gly Asn Leu Thr Val Ile Tyr Thr Phe Cys Arg
                85                  90                  95

Asn Arg Gly Leu Arg Thr Pro Ala Asn Met Phe Ile Ile Asn Leu Ala
                100                 105                 110

Val Ser Asp Phe Leu Met Ser Val Thr Gln Ala Pro Val Phe Phe Ala
            115                 120                 125

Ser Ser Leu Tyr Lys Lys Trp Leu Phe Gly Glu Thr Gly Cys Glu Phe
        130                 135                 140

Tyr Ala Phe Cys Gly Ala Val Phe Gly Ile Thr Ser Met Ile Thr Leu
145                 150                 155                 160
```

```
Thr Ala Ile Ala Met Asp Arg Ile Tyr Arg Ile Phe Glu Gln Gly Lys
            165                 170                 175
Arg Ser Val Thr Pro Pro Phe Ile Ser Pro Thr Ser Gln Val Leu
        180                 185                 190
Leu Gly Val Trp Leu Tyr Ala Leu Ala Trp Ser Leu Pro Pro Phe Phe
    195                 200                 205
Gly Trp Ser Ala Tyr Val Pro Glu Gly Leu Leu Thr Ser Cys Ser Trp
        210                 215                 220
Asp Tyr Met Thr Phe Thr Pro Gln Val Arg Ala Tyr Thr Met Leu Leu
225                 230                 235                 240
Phe Cys Phe Val Phe Phe Leu Pro Leu Leu Ile Ile Ile Phe Cys Tyr
                245                 250                 255
Ile Phe Ile Phe Arg Ala Arg Gly Val Pro Glu Thr Phe Asn Glu Ala
            260                 265                 270
Lys Val Ala Leu Ile Val Ile Leu Leu Phe Val Leu Ser Trp Ala Pro
    275                 280                 285
Tyr Ser Thr Val Ala Leu Val Ala Phe Ala Gly Tyr Ser His Ile Leu
        290                 295                 300
Thr Pro Tyr Met Ser Ser Val Pro Ala Val Ile Ala Lys Ala Ser Ala
305                 310                 315                 320
Ile His Asn Pro Ile Ile Tyr Ala Ile Thr His Pro Glu Gln Asn Val
                325                 330                 335
Gln Lys Arg Lys Arg Ser Leu Lys Lys Thr Ser Thr Met Ala Ala Pro
            340                 345                 350
Pro Lys Ser Glu Asn Ser Glu Asp Ala Lys
            355                 360

<210> SEQ ID NO 9
<211> LENGTH: 1101
<212> TYPE: DNA
<213> ORGANISM: Mus sp.

<400> SEQUENCE: 9
atggactctc cttcaggacc aagagtcttg tcaagcttaa ctcaggatcc cagcttcaca      60
accagtcctg ccctgcaagg catttggaac ggcactcaga acgtctccgt aagagcccag     120
cttctctctg ttagccccac gacatctgca catcaggctg ctgcctgggt cccctccccc     180
acagtcgatg tcccagacca tgctcactat accctaggca cggtgatcct gctggtggga     240
ctcacaggga tgctgggcaa tctgacggtc atctacacct tcatgcgaca aacgacact     300
cccatagtcc gcgcctctgg ccgtgagctt ttcatcatca acctcgcagt cagcgacttc     360
ctcatgtcag tcactcaggc cccggtcttc tttgccagca gcctctacaa gaagtggctc     420
tttggggaga caggttgcga gttctatgcc ttctgcgggg ctgtctttgg catcacttcc     480
atgatcaccc tgacagccat agccatggac cgcatctacc gcattttcga gcaagggaag     540
cgctctgtca cgccgccacc cttcatcagc ccacctcgc aggtcctgct aggcgtctgg     600
ctttatgccc tggcctggag tctgccacct ttctttggtt ggagtgccta cgtgcccgag     660
gggctgctga catcctgctc ctgggactac atgaccttca cccccaggt gcgtgcctac     720
accatgctgc tcttctgctt tgtcttcttc ctcccctgc tcatcatcat cttctgctac     780
atcttcatct tcagggcccg aggtgtgcca gagaccttca tgaagccaa ggtcgcactg     840
attgtcattc ttctcttcgt gctgtcctgg gctcccttact ccactgtggc tctggtggcc     900
tttgctggat actcgcacat cctgacgccc tacatgagct cggtgccagc cgtcatcgcc     960
```

```
aaggcttctg ccatccacaa tcccattatc tacgccatca ctcaccccga gcagaacgtg    1020
cagaagcgga agcgcagcct caagaagacc tccacgatgg cggccccgcc caagagcgag    1080
aactcagagg acgccaagta g                                              1101
```

<210> SEQ ID NO 10
<211> LENGTH: 366
<212> TYPE: PRT
<213> ORGANISM: Mus sp.

<400> SEQUENCE: 10

```
Met Asp Ser Pro Ser Gly Pro Arg Val Leu Ser Ser Leu Thr Gln Asp
1               5                   10                  15

Pro Ser Phe Thr Thr Ser Pro Ala Leu Gln Gly Ile Trp Asn Gly Thr
            20                  25                  30

Gln Asn Val Ser Val Arg Ala Gln Leu Leu Ser Val Ser Pro Thr Thr
        35                  40                  45

Ser Ala His Gln Ala Ala Ala Trp Val Pro Phe Pro Thr Val Asp Val
    50                  55                  60

Pro Asp His Ala His Tyr Thr Leu Gly Thr Val Ile Leu Leu Val Gly
65                  70                  75                  80

Leu Thr Gly Met Leu Gly Asn Leu Thr Val Ile Tyr Thr Phe Met Arg
                85                  90                  95

His Asn Asp Thr Pro Ile Val Arg Ala Ser Gly Arg Glu Leu Phe Ile
            100                 105                 110

Ile Asn Leu Ala Val Ser Asp Phe Leu Met Ser Val Thr Gln Ala Pro
        115                 120                 125

Val Phe Phe Ala Ser Ser Leu Tyr Lys Lys Trp Leu Phe Gly Glu Thr
    130                 135                 140

Gly Cys Glu Phe Tyr Ala Phe Cys Gly Ala Val Phe Gly Ile Thr Ser
145                 150                 155                 160

Met Ile Thr Leu Thr Ala Ile Ala Met Asp Arg Ile Tyr Arg Ile Phe
                165                 170                 175

Glu Gln Gly Lys Arg Ser Val Thr Pro Pro Phe Ile Ser Pro Thr
            180                 185                 190

Ser Gln Val Leu Leu Gly Val Trp Leu Tyr Ala Leu Ala Trp Ser Leu
        195                 200                 205

Pro Pro Phe Phe Gly Trp Ser Ala Tyr Val Pro Glu Gly Leu Leu Thr
    210                 215                 220

Ser Cys Ser Trp Asp Tyr Met Thr Phe Thr Pro Gln Val Arg Ala Tyr
225                 230                 235                 240

Thr Met Leu Leu Phe Cys Phe Val Phe Phe Leu Pro Leu Leu Ile Ile
                245                 250                 255

Ile Phe Cys Tyr Ile Phe Ile Phe Arg Ala Arg Gly Val Pro Glu Thr
            260                 265                 270

Phe Asn Glu Ala Lys Val Ala Leu Ile Val Ile Leu Leu Phe Val Leu
        275                 280                 285

Ser Trp Ala Pro Tyr Ser Thr Val Ala Leu Val Ala Phe Ala Gly Tyr
    290                 295                 300

Ser His Ile Leu Thr Pro Tyr Met Ser Ser Val Pro Ala Val Ile Ala
305                 310                 315                 320

Lys Ala Ser Ala Ile His Asn Pro Ile Ile Tyr Ala Ile Thr His Pro
                325                 330                 335

Glu Gln Asn Val Gln Lys Arg Lys Arg Ser Leu Lys Lys Thr Ser Thr
            340                 345                 350
```

```
Met Ala Ala Pro Pro Lys Ser Glu Asn Ser Glu Asp Ala Lys
        355                 360                 365
```

```
<210> SEQ ID NO 11
<211> LENGTH: 14
<212> TYPE: PRT
<213> ORGANISM: Homo sapiens

<400> SEQUENCE: 11

Phe Ile Ser Pro Thr Ser Gln Val Leu Leu Gly Val Trp Leu
1               5                   10
```

```
<210> SEQ ID NO 12
<211> LENGTH: 14
<212> TYPE: PRT
<213> ORGANISM: Homo sapiens

<400> SEQUENCE: 12

Tyr Ile Phe Ile Phe Arg Ala Arg Gly Val Pro Glu Thr Phe
1               5                   10
```

```
<210> SEQ ID NO 13
<211> LENGTH: 17
<212> TYPE: PRT
<213> ORGANISM: Homo sapiens

<400> SEQUENCE: 13

Tyr Ile Phe Ile Phe Arg Ala Ile Lys Ala Arg Gly Val Pro Glu Thr
1               5                   10                  15

Phe
```

```
<210> SEQ ID NO 14
<211> LENGTH: 14
<212> TYPE: PRT
<213> ORGANISM: Homo sapiens

<400> SEQUENCE: 14

Glu Thr Phe Asn Glu Ala Lys Ile Met Leu Leu Val Ile Leu
1               5                   10
```

```
<210> SEQ ID NO 15
<211> LENGTH: 14
<212> TYPE: PRT
<213> ORGANISM: Homo sapiens

<400> SEQUENCE: 15

Ile Tyr Ala Ile Thr His Pro Glu Gln Asn Val Gln Lys Arg
1               5                   10
```

```
<210> SEQ ID NO 16
<211> LENGTH: 4
<212> TYPE: PRT
<213> ORGANISM: Homo sapiens

<400> SEQUENCE: 16

Asp Arg Ile Tyr
1
```

```
<210> SEQ ID NO 17
<211> LENGTH: 4
<212> TYPE: PRT
<213> ORGANISM: Homo sapiens

<400> SEQUENCE: 17
```

Asn Arg Ile Tyr
1

<210> SEQ ID NO 18
<211> LENGTH: 14
<212> TYPE: PRT
<213> ORGANISM: Artificial Sequence
<220> FEATURE:
<223> OTHER INFORMATION: splicing ligation site

<400> SEQUENCE: 18

Phe Ile Ser Pro Thr Ser Gln Val Leu Leu Gly Val Trp Leu
1               5                   10

<210> SEQ ID NO 19
<211> LENGTH: 14
<212> TYPE: PRT
<213> ORGANISM: Artificial Sequence
<220> FEATURE:
<223> OTHER INFORMATION: splicing ligation site

<400> SEQUENCE: 19

Tyr Ile Phe Ile Phe Arg Ala Arg Gly Val Pro Glu Thr Phe
1               5                   10

<210> SEQ ID NO 20
<211> LENGTH: 17
<212> TYPE: PRT
<213> ORGANISM: Artificial Sequence
<220> FEATURE:
<223> OTHER INFORMATION: splicing ligation site

<400> SEQUENCE: 20

Tyr Ile Phe Ile Phe Arg Ala Ile Lys Ala Arg Gly Val Pro Glu Thr
1               5                   10                  15

Phe

<210> SEQ ID NO 21
<211> LENGTH: 14
<212> TYPE: PRT
<213> ORGANISM: Artificial Sequence
<220> FEATURE:
<223> OTHER INFORMATION: splicing ligation site

<400> SEQUENCE: 21

Glu Thr Phe Asn Glu Ala Lys Ile Met Leu Leu Val Ile Leu
1               5                   10

<210> SEQ ID NO 22
<211> LENGTH: 13
<212> TYPE: PRT
<213> ORGANISM: Artificial Sequence
<220> FEATURE:
<223> OTHER INFORMATION: splicing ligation site

<400> SEQUENCE: 22

Tyr Ala Ile Thr His Pro Glu Gln Asn Val Gln Lys Arg
1               5                   10